US011559282B2

(12) United States Patent
Sugiyama

(10) Patent No.: US 11,559,282 B2
(45) Date of Patent: Jan. 24, 2023

(54) MEDICAL INFORMATION PROCESSING SYSTEM AND MEDICAL IMAGE PROCESSING APPARATUS

(71) Applicant: CANON MEDICAL SYSTEMS CORPORATION, Otawara (JP)

(72) Inventor: Atsuko Sugiyama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 301 days.

(21) Appl. No.: 15/889,582

(22) Filed: Feb. 6, 2018

(65) Prior Publication Data
US 2018/0220994 A1 Aug. 9, 2018

(30) Foreign Application Priority Data

Feb. 6, 2017 (JP) .............................. JP2017-019683

(51) Int. Cl.
A61B 8/00 (2006.01)
A61B 6/00 (2006.01)
(Continued)

(52) U.S. Cl.
CPC .............. A61B 8/463 (2013.01); A61B 6/025 (2013.01); A61B 6/0414 (2013.01);
(Continued)

(58) Field of Classification Search
CPC . G06T 2207/10016; G06T 2207/10132; G06T 7/0012; G06T 2207/30068;
(Continued)

(56) References Cited

U.S. PATENT DOCUMENTS 9,171,130 B2 * 10/2015 Gustafson ............. G06F 3/0482
2004/0204965 A1 * 10/2004 Gueck ................... G16H 30/20
705/3
(Continued)

FOREIGN PATENT DOCUMENTS

CN 104303184 A 1/2015
JP 2001-125999 A1 5/2001
(Continued)

OTHER PUBLICATIONS http://www.medience.co_jp/information/pdf/09-17.pdf, vol. 09-17, May 2009, 6 Pages (with Partial English Translation).
(Continued)

Primary Examiner — Christopher Koharski
Assistant Examiner — Renee C Langhals
(74) Attorney, Agent, or Firm — Oblon, McClelland, Maier & Neustadt, L.L.P.

(57) ABSTRACT

A medical information processing system in an embodiment includes processing circuitry. The processing circuitry acquires an ultrasound image including an observation target and having additional information, positional information indicating a position of an ultrasound probe in a subject at time of collection of the ultrasound image, and a reference image obtained by taking an image of a region including the observation target at a time point other than the time of collection. The processing circuitry generates, based on the positional information, correspondence information in which the ultrasound image and the reference image are associated with each other. The processing circuitry causes an output unit to output the generated correspondence information.

13 Claims, 23 Drawing Sheets

(51) Int. Cl.
*A61B 8/08* (2006.01)
*A61B 6/02* (2006.01)
*A61B 6/04* (2006.01)

(52) U.S. Cl.
CPC ............ *A61B 6/4417* (2013.01); *A61B 6/463* (2013.01); *A61B 6/464* (2013.01); *A61B 6/502* (2013.01); *A61B 6/5247* (2013.01); *A61B 8/0825* (2013.01); *A61B 8/0841* (2013.01); *A61B 8/4263* (2013.01); *A61B 8/4416* (2013.01); *A61B 8/5207* (2013.01); *A61B 8/488* (2013.01)

(58) Field of Classification Search
CPC .. G01N 33/5091; A61B 8/463; A61B 8/0841; A61B 8/5207; A61B 8/4416; A61B 8/0825; A61B 6/4417; A61B 6/464; A61B 6/5247; A61B 6/025; A61B 6/0414; A61B 6/463; A61B 8/4263; A61B 6/502; A61B 8/488; A61B 8/52
USPC ........................................................ 600/461
See application file for complete search history.

(56) References Cited

U.S. PATENT DOCUMENTS

| | | | | |
|---|---|---|---|---|
| 2005/0089205 A1* | 4/2005 | Kapur | ................... | A61B 8/5238 382/128 |
| 2011/0125526 A1 | 5/2011 | Gustafson | | |
| 2013/0289405 A1* | 10/2013 | Wang | ................... | A61B 6/5247 600/440 |
| 2014/0082542 A1* | 3/2014 | Zhang | ................... | G16H 30/40 715/771 |
| 2015/0097868 A1* | 4/2015 | Banerjee | ................ | G16H 30/20 345/634 |
| 2015/0139518 A1* | 5/2015 | Oohashi | ................ | G06T 7/0016 382/131 |
| 2015/0146855 A1* | 5/2015 | Futamura | ............. | A61B 8/0825 378/63 |
| 2015/0178921 A1* | 6/2015 | Hashimoto | ............ | A61B 8/469 382/131 |
| 2015/0221091 A1* | 8/2015 | Sugiyama | ............ | A61B 8/5261 382/131 |
| 2016/0074012 A1* | 3/2016 | Forzoni | ................ | A61B 8/4245 600/440 |
| 2016/0110875 A1* | 4/2016 | Sugiyama | ............. | G06T 7/0012 382/131 |
| 2016/0374644 A1* | 12/2016 | Mauldin, Jr. | ........ | A61B 8/5223 600/424 |
| 2017/0000462 A1* | 1/2017 | Washburn | ............ | A61B 8/0891 |

FOREIGN PATENT DOCUMENTS

| | | |
|---|---|---|
| JP | 2012-528649 A1 | 11/2012 |
| JP | 2015-027450 | 2/2015 |
| KR | 20100018886 A * | 2/2010 |

OTHER PUBLICATIONS http://www.ctjsc.com/ctjsc_cms/wp-content/uploads/lecture2_pdf , Lecture of Breast Ultrasound, 5 Pages (with Partial English Translation).

"Echo scan guide for supporting mammary gland ultrasonography," http://www.innervision.co.jp/acl/suite/toshiba/technical_notes/160855 , Oct. 2017, 4 Pages (with Partial English Translation).

Combined Chinese Office Action and Search Report dated Jul. 9, 2020 in Patent Application No. 201810116829.6 (with English translation of Categories of Cited Documents), 12 pages.

Japanese Office Action dated Oct. 6, 2020, issued in Japanese Patent Application No. 2017-019683.

Office Action dated Jan. 28, 2021 in corresponding Chinese Patent Application No. 201810116829.6, 9 pages.

Chinese Office Action dated Aug. 18, 2021, issued in Chinese Patent Application No. 201810116829.6.

Chinese Office Action dated Mar. 9, 2022, issued in Chinese Patent Application No. 201810116829.6.

* cited by examiner

FIG.6
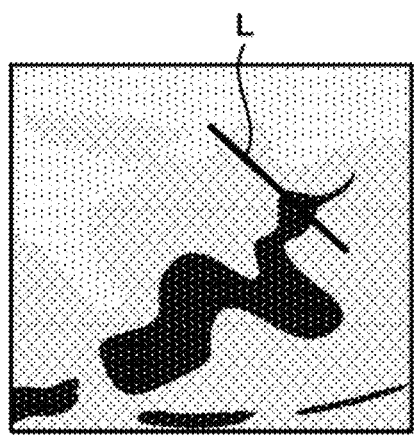
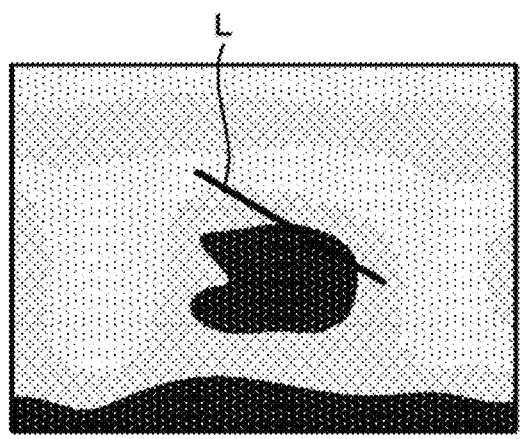
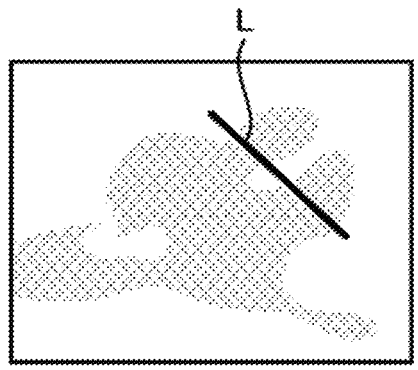
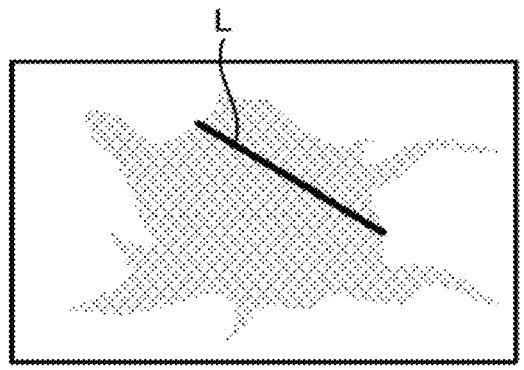

MEDICAL INFORMATION PROCESSING SYSTEM AND MEDICAL IMAGE PROCESSING APPARATUS

CROSS-REFERENCE TO RELATED APPLICATIONS

This application is based upon and claims the benefit of priority from Japanese Patent Application No. 2017-019683, filed on Feb. 6, 2017; the entire contents of which are incorporated herein by reference.

FIELD

Embodiments described herein relate generally to a medical information processing system and a medical image processing apparatus.

BACKGROUND

Conventionally, in breast cancer clinical practice, specimens obtained by biopsy are used for pathological diagnosis. For example, specimens from ultrasound-guided biopsy are sent by a radiologist or a breast surgeon to a pathologist together with an ultrasound image and a pathological examination request. Then, the pathologist receives the specimen, the ultrasound image, and the pathological examination request, and performs a pathological diagnosis. For example, the pathologist grasps the whole picture from an ultrasound image of a subject. For a pathological diagnosis using a pathological image, the pathologist performs a diagnosis by adding a finding from the ultrasound image to a finding from the pathological image in consideration of consistency between the ultrasound image and the pathological image.

BRIEF DESCRIPTION OF THE DRAWINGS

FIG. 6 is a diagram for describing the related art;

DETAILED DESCRIPTION

According to an embodiment, a medical information processing system includes processing circuitry. The processing circuitry is configured to acquire an ultrasound image including an observation target and having additional information, positional information indicating a position of an ultrasound probe in a subject at time of collection of the ultrasound image, and a reference image obtained by taking an image of a region including the observation target at a time point other than the time of collection. The processing circuitry is configured to generate, based on the positional information, correspondence information in which the ultrasound image and the reference image are associated with each other. The processing circuitry is configured to cause a display to output the generated correspondence information.

Referring to the accompanying drawings, a medical information processing system and a medical image processing apparatus according to embodiments are described below. The embodiments are not limited to the following embodiments. Contents described in one embodiment are similarly applied to other embodiments in principle.

First Embodiment

Figure 1:
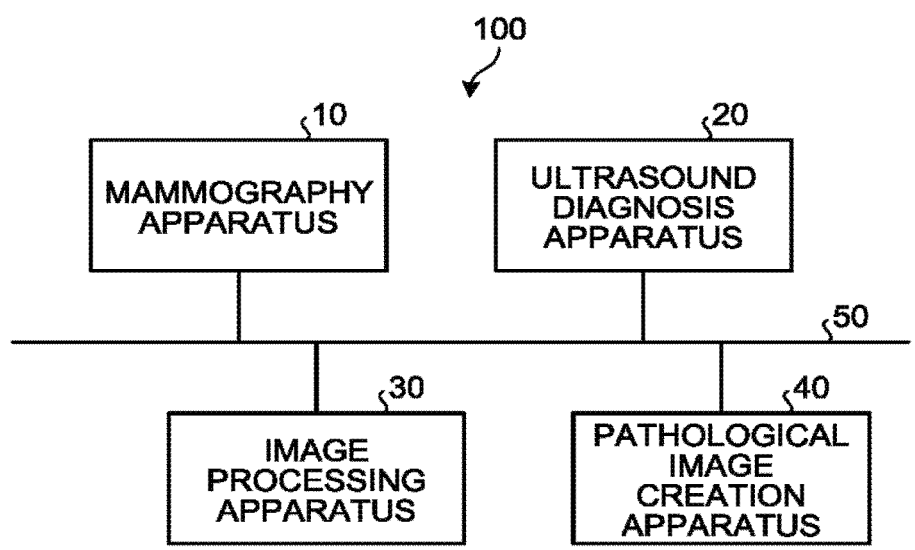
FIG. 1 is a diagram illustrating a configuration example of a medical information processing system according to a first embodiment.

FIG. 1 is a diagram illustrating a configuration example of a medical information processing system 100 according to a first embodiment. For example, the medical information processing system 100 according to the first embodiment is installed in a hospital for breast cancer clinical practice, and is used for pathological diagnosis of mammary gland involving ultrasound image-guided biopsy. As illustrated in FIG. 1, the medical information processing system 100 according to the first embodiment includes, for example, a mammography apparatus 10, an ultrasound diagnosis apparatus 20, an image processing apparatus 30, and a pathological image creation apparatus 40. The apparatuses are connected to one another through a network 50, and mutually transmit and receive images taken by the mammography apparatus 10 and the ultrasound diagnosis apparatus 20. For example, when a picture archiving and communication system (PACS) is introduced to the medical information processing system 100, the apparatuses mutually transmit and receive medical images in the format of digital imaging and communications in medicine (DICOM) obtained by adding additional information to medical images. Examples of the additional information include subject identifiers (IDs) for identifying subjects, examination IDs for identifying examinations, apparatus IDs for identifying apparatus, and series IDs for identifying single photographing by apparatus.

The mammography apparatus 10 irradiates a breast of a subject with X rays, and detects X rays transmitted through the breast to generate a mammography image. For example, the mammography apparatus 10 generates a mammography image (MLO image) based on X-ray projection data generated by outputting X rays from a mediolateral-oblique (MLO) direction without changing the angle to the breast. For example, the mammography apparatus 10 generates a mammography image (CC image) based on X-ray projection data generated by outputting X rays from a cranio-caudal (CC) direction without changing the angle to the breast.

The mammography apparatus 10 generates a tomosynthesis image, which is a three-dimensional image, based on images of a subject photographed from various angles. For example, the mammography apparatus 10 generates a tomosynthesis image (MLO tomosynthesis image) based on X-ray projection data generated by outputting X rays from the MLO direction while changing the angle to the breast. For example, the mammography apparatus 10 generates a tomosynthesis image (CC tomosynthesis image) based on X-ray projection data generated by outputting X rays from the CC direction while changing the angle to the breast. Specifically, the mammography apparatus 10 generates a tomosynthesis image through predetermined processing based on images corresponding to angles to the subject. Examples of the predetermined processing include shift-and-add method and filtered back projection (FBP) method. In the following, the term "mammography image" includes an MLO tomosynthesis image and a CC tomosynthesis image in addition to an MLO image and a CC image. For discrimination from a tomosynthesis image, an MLO image and a CC image are referred to as "two-dimensional mammography images". For example, the MLO image is referred to as "two-dimensional MLO image" and the CC image is referred to as "two-dimensional CC image". Information indicating a photographing direction is provided to additional information for a tomosynthesis image. Examples of the information indicating the photographing direction as used herein include positional information represented by an apparatus coordinate system of the mammography apparatus 10. When a mammography image is generated by the mammography apparatus 10, the information indicating the photographing direction is provided to the mammography image as additional information.

Referring back to FIG. 1, the ultrasound diagnosis apparatus 20 generates an ultrasound image based on reflected wave data collected by scanning the subject with an ultrasound probe configured to transmit and receive ultrasound waves.

Figure 2:
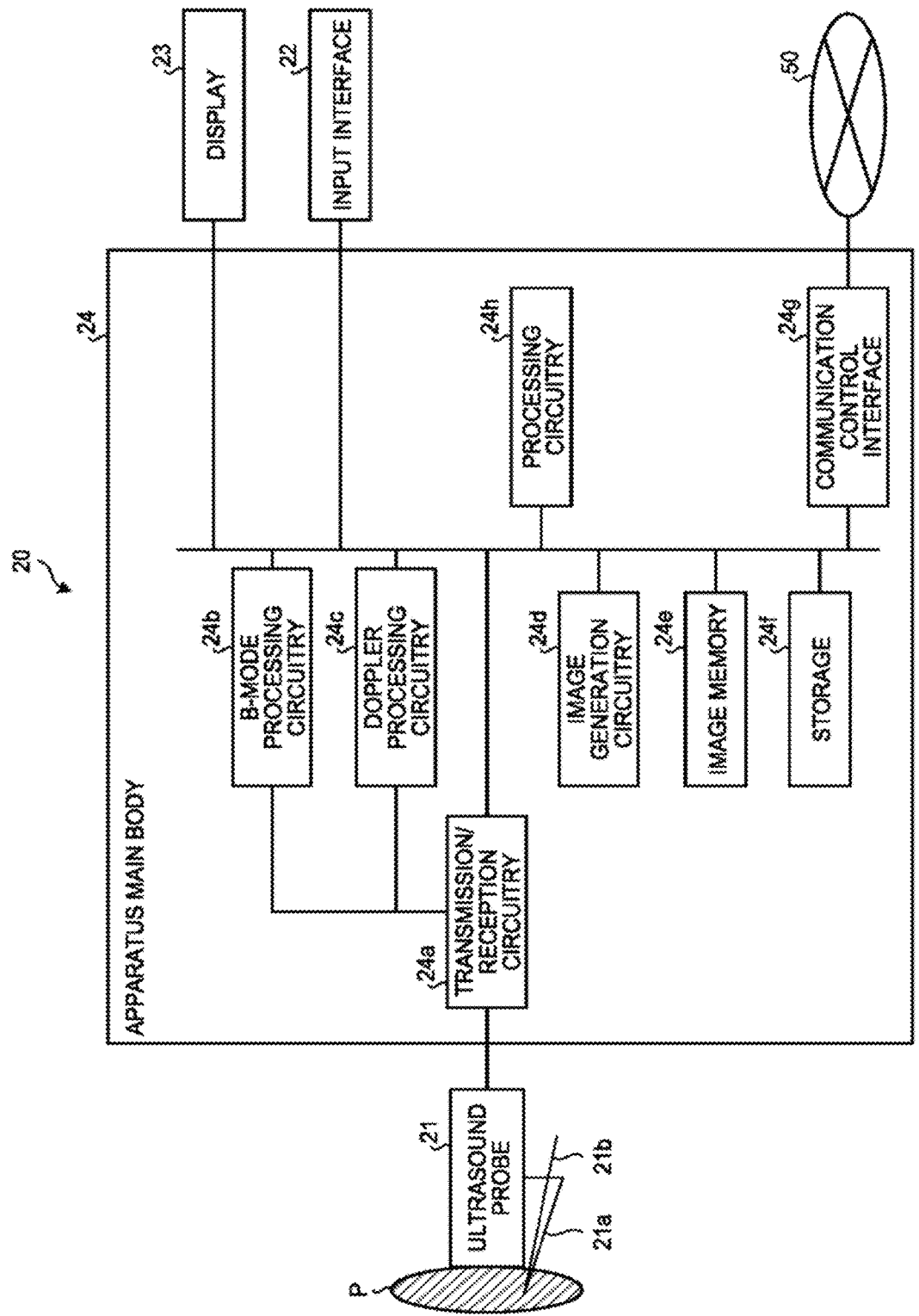
FIG. 2 is a diagram illustrating a configuration example of an ultrasound diagnosis apparatus according to the first embodiment.

FIG. 2 is a diagram illustrating a configuration example of the ultrasound diagnosis apparatus 20 according to the first embodiment. As illustrated in FIG. 2, the ultrasound diagnosis apparatus 20 according to the first embodiment includes an ultrasound probe 21, an input interface 22, a display 23, and an apparatus main body 24. The ultrasound probe 21 is communicably connected to transmission/reception circuitry 24a included in the apparatus main body 24 described later. The input interface 22 and the display 23 are communicably connected to various circuits included in the apparatus main body 24.

The ultrasound probe 21 is brought into contact with the body surface of a subject P to transmit and receive ultrasound waves. For example, the ultrasound probe 21 includes piezoelectric transducer elements (also referred to as "transducer elements"). The piezoelectric transducer elements generate ultrasound waves based on a transmission signal supplied from the transmission/reception circuitry 24a. The generated ultrasound waves are reflected in tissue in the body of the subject P, and are received by the piezoelectric transducer elements as a reflected wave signal. The ultrasound probe 21 transmits the reflected wave signal received by the piezoelectric transducer elements to the transmission/reception circuitry 24a.

The first embodiment is applicable to both the case where the ultrasound probe 21 is a 1D array probe configured to scan a two-dimensional region in the subject P (two-dimensional scan) and the case where the ultrasound probe 21 is a mechanical 4D probe or a 2D array probe configured to scan a three-dimensional region in the subject P (three-dimensional scan).

In addition, a puncture adapter 21a is mounted to the ultrasound probe 21 according to the first embodiment. Then, a puncture needle 21b is mounted to the puncture adapter 21a. An operator such as a doctor or an engineer inserts the puncture needle 21b mounted to the puncture adapter 21a up to a target site in the subject P while referring to an ultrasound image, thereby performing biopsy for collecting examination materials for the purpose of pathological diagnosis.

Figure 3:
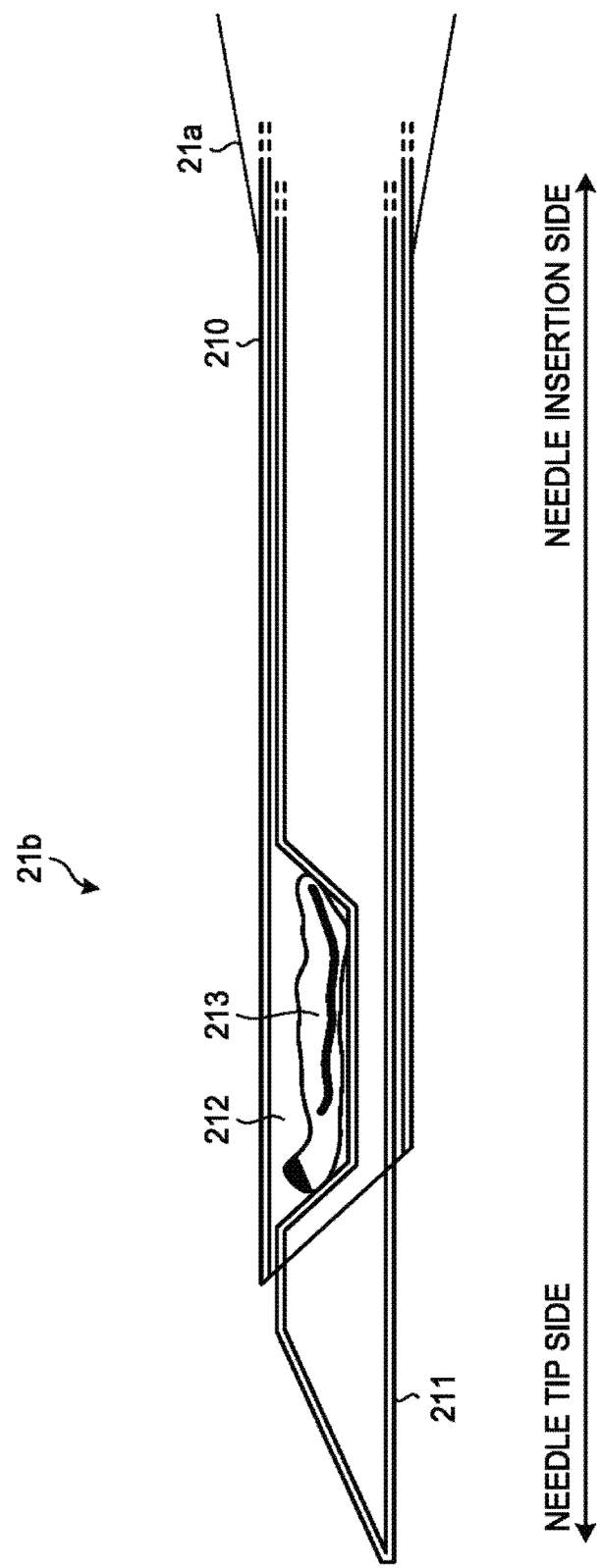
FIG. 3 is a diagram for describing a puncture needle according to the first embodiment.

FIG. 3 is a diagram for describing the puncture needle 21b according to the first embodiment. As illustrated in FIG. 3, the puncture needle 21b includes an outer cylinder 210, an inner needle 211, and a sample notch 212. One side of the puncture needle 21b on the inner needle 211 side is referred to as "needle tip side" and the other side on the puncture adapter 21a side is referred to as "needle insertion side".

The outer cylinder 210 moves from the needle insertion side to the needle tip side in response to an operation by the operator. When the outer cylinder 210 moves, a partial region of the target site is cut as a specimen 213 by the outer cylinder 210 and the inner needle 211, and the cut specimen 213 is collected in the sample notch 212. The collected specimen 213 is used to create a pathological image. The creation of the pathological image is described later.

Referring back to FIG. 2, for example, the input interface 22 corresponds to a mouse, a keyboard, a button, a panel switch, a touch command screen, a foot switch, a trackball, or a joystick. The input interface 22 receives various kinds of setting requests from the operator of the ultrasound diagnosis apparatus 20, and transfers the received various kinds of setting requests to the circuits in the apparatus main body 24 as appropriate.

The display 23 displays a graphical user interface (GUI) used for the operator to input various kinds of setting requests by using the input interface 22, and displays ultrasound images generated by the apparatus main body 24.

The apparatus main body 24 is an apparatus configured to generate ultrasound images based on reflected wave signals received by the ultrasound probe 21. As illustrated in FIG.

2, the apparatus main body 24 includes, for example, the transmission/reception circuitry 24a, B-mode processing circuitry 24b, Doppler processing circuitry 24c, image generation circuitry 24d, an image memory 24e, a storage 24f, a communication control interface 24g, and processing circuitry 24h. The transmission/reception circuitry 24a, the B-mode processing circuitry 24b, the Doppler processing circuitry 24c, the image generation circuitry 24d, the image memory 24e, the storage 24f, the communication control interface 24g, and the processing circuitry 24h are communicably connected to one another.

The transmission/reception circuitry 24a controls the transmission and reception of ultrasound waves performed by the ultrasound probe 21. For example, the transmission/reception circuitry 24a controls the transmission and reception of ultrasound waves performed by the ultrasound probe 21 based on an instruction from the processing circuitry 24h described later. The transmission/reception circuitry 24a creates transmission waveform data, and generates a transmission signal used for the ultrasound probe 21 to transmit ultrasound waves based on the created transmission waveform data. Then, the transmission/reception circuitry 24a applies the transmission signal to the ultrasound probe 21, thereby causing the ultrasound probe 21 to transmit an ultrasound beam obtained by focusing ultrasound waves into a beam.

The transmission/reception circuitry 24a performs addition processing by adding a predetermined delay time to the reflected wave signal received by the ultrasound probe 21, thereby generating reflected wave data in which components of the reflected wave signal that are reflected from a direction corresponding to reception directivity are emphasized. The transmission/reception circuitry 24a transmits the generated reflected wave data to the B-mode processing circuitry 24b and the Doppler processing circuitry 24c.

For example, the transmission/reception circuitry 24a includes an amplifier circuit (referred to as "Amp" as appropriate), an analog/digital (A/D) converter (referred to as "ADC" as appropriate), a generation circuit, and a quadrature detection circuit (referred to as "IQ" as appropriate). The amplifier circuit performs gain correction processing by amplifying the reflected wave signal for each channel. The A/D converter performs A/D conversion of the gain-corrected reflected wave signal.

The generation circuit gives digital data a reception delay time necessary for determining reception directivity. Then, the generation circuit performs addition processing of the reflected wave signal having the reception delay time. As a result of the addition processing by the generation circuit, the components of the reflected wave signal that are reflected from the direction corresponding to the reception directivity are emphasized.

Then, the quadrature detection circuit converts the output signal of the adder into an in-phase signal (I signal, I: In-phase) and a quadrature signal (Q signal, Q: Quadrature-phase) in a base bandwidth. Then, the quadrature detection circuit stores the I signal and the Q signal (hereinafter referred to as "IQ signals") in a buffer as reflected wave data. The quadrature detection circuit may store the output signal of the adder in the buffer after converting the output signal into radio frequency (RF) signals. The IQ signals or the RF signals are signals (reception signals) including phase information. In the above description, the quadrature detection circuit is disposed at the subsequent stage of the generation circuit, but the embodiments are not limited thereto. For example, the quadrature detection circuit may be disposed at the preceding stage of the generation circuit. In such a case, the generation circuit performs addition processing of an I signal and a Q signal.

The B-mode processing circuitry 24b performs various kinds of signal processing on the reflected wave data generated from the reflected wave signal by the transmission/reception circuitry 24a. The B-mode processing circuitry 24b subjects the reflected wave data received from the transmission/reception circuitry 24a to processing such as logarithmic amplification and envelope detection, thereby generating data (B-mode data) in which signal intensity at each sample point (observation point) is represented by the level of luminance. The B-mode processing circuitry 24b transmits the generated B-mode data to the image generation circuitry 24d.

The Doppler processing circuitry 24c generates, from the reflected wave data received from the transmission/reception circuitry 24a, data (Doppler data) in which motion information on a moving object based on Doppler effect is extracted at each sample point in a scanning region. Specifically, the Doppler processing circuitry 24c generates Doppler data in which an average velocity, a variance, or a power value is extracted at each sample point as motion information of the moving object. Examples of the moving object include a bloodstream, tissue such as the wall of the heart, and a contrast agent. The Doppler processing circuitry 24c transmits the generated Doppler data to the image generation circuitry 24d.

The image generation circuitry 24d generates ultrasound images from the data generated by the B-mode processing circuitry 24b and the Doppler processing circuitry 24c. For example, the image generation circuitry 24d generates a B-mode image in which the intensity of reflected waves is represented by luminance from the B-mode data generated by the B-mode processing circuitry 24b. The image generation circuitry 24d generates a Doppler image representing moving object information from the Doppler data generated by the Doppler processing circuitry 24c. The Doppler image is a velocity image, a variance image, a power image, or a combination thereof.

The image memory 24e is a memory configured to store therein data generated by the B-mode processing circuitry 24b, the Doppler processing circuitry 24c, and the image generation circuitry 24d. For example, an operator can invoke images recorded during an examination after a diagnosis, and reproduce the image as a still image or moving images. The image memory 24e may store therein image luminance signals that have passed the transmission/reception circuitry 24a, other raw data, and images acquired through the network 50.

The storage 24f stores therein device control programs for transmitting and receiving ultrasound waves and performing image processing and display processing and various kinds of data such as diagnosis information (for example, subject IDs and doctor's findings), diagnosis protocols, and various kinds of setting information. The storage 24f may be used to store images stored in the image memory 24e. Data stored in the storage 24f can be transferred to an external device through an interface (not shown).

Figure 4:
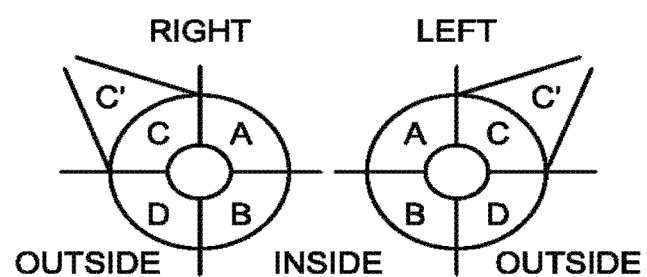
FIG. 4 is a diagram illustrating an example of a body mark according to the first embodiment.

The storage 24f stores body marks therein. FIG. 4 is a diagram illustrating an example of the body marks according to the first embodiment. In the example illustrated in FIG. 4, a schematic diagram of mammary gland regions is illustrated as an example of the body marks schematically illustrating breasts. For example, as illustrated in FIG. 4, the schematic diagram of the mammary gland regions has, for each of the right and left breasts, a circular region representing the region of the breast (hereinafter referred to as "breast region") and a substantially triangular region representing the region of the axilla (hereinafter referred to as "axillary region").

The circular region representing the breast region is vertically and horizontally divided into four regions of "A" to "D", for example. For example, the region of "A" (hereinafter referred to as "region A") represents an inner upper region of the breast, and the region of "B" (hereinafter referred to as "region B") represents an inner lower region of the breast. For example, the region of "C" (hereinafter referred to as "region C") represents an outer upper region of the breast, and the region of "D" (hereinafter referred to as "region D") represents an outer lower region of the breast. A substantially triangular region "C'" (hereinafter referred to as "region C'") representing the axillary region has a shape that extends obliquely upward from the region C and becomes narrower as the distance from the region C increases. For example, a region of "E" (hereinafter referred to as "region E"), which is not illustrated in FIG. 4, represents a region of the areola. Various kinds of diagrams can be used as the schematic diagram as long as the diagram represents the positional relation in the breasts. In FIG. 4, an example in which the region of the breast is divided into four regions is illustrated, but the embodiments are not limited thereto. The region of the breast may be represented by a method other than the method of dividing the region into four.

Referring back to FIG. 2, the communication control interface 24g controls communication performed between the ultrasound diagnosis apparatus 20 and another apparatus through the network 50. For example, the communication control interface 24g transfers ultrasound images generated by the image generation circuitry 24d to another apparatus through the network 50. The ultrasound images transferred through the network 50 can be used for image display or image processing in the apparatus at the transfer destination.

The processing circuitry 24h controls overall processing of the ultrasound diagnosis apparatus 20. Specifically, the processing circuitry 24h controls processing of the transmission/reception circuitry 24a, the B-mode processing circuitry 24b, the Doppler processing circuitry 24c, and the image generation circuitry 24d based on various kinds of setting requests input from the operator through the input interface 22 and various kinds of control programs and various kinds of data read from the storage 24f. The processing circuitry 24h causes the display 23 to display ultrasound image data stored in the image memory 24e.

The processing circuitry 24h generates scanning positional information in which the position of the ultrasound probe 21 obtained when the breast of the subject P is scanned by using the ultrasound probe 21 is associated on a schematic diagram of the breast. For example, the processing circuitry 24h generates scanning positional information in which a probe mark schematically representing the ultrasound probe 21 is superimposed on the schematic diagram at the position of the ultrasound probe 21 during ultrasound wave scanning. Specifically, the scanning positional information is obtained by providing information indicating the ultrasound probe 21 at a position corresponding to a scanning site on the schematic diagram representing the scanning site.

More specifically, the processing circuitry 24h receives the arrangement of the probe mark on the schematic diagram from the operator through the input interface 22. The operator arranges the probe mark at a position on the schematic diagram corresponding to the position of the ultrasound probe 21 during ultrasound wave scanning. In response thereto, the processing circuitry 24h generates scanning positional information. The processing circuitry 24h causes the storage 24f to store the generated scanning positional information. The processing circuitry 24h causes the storage 24f to store identification information (subject ID) that can uniquely identify the subject associated with the scanning positional information. In other words, the storage 24f stores identification information that can uniquely identify the subject in association with scanning positional information obtained by providing the position of a region of interest to the schematic diagram of the breast. For example, the processing circuitry 24h causes the storage 24f to store therein the scanning positional information in the DICOM format or the Joint Photographic Experts Group (JPEG) format. In other words, for example, the storage 24f stores therein the scanning positional information in the DICOM format or the JPEG format. The processing circuitry 24h may add the scanning positional information as additional information for ultrasound images and cause the storage 24f to store therein the resultant. The scanning positional information may be stored in a format other than the DICOM format and the JPEG format. For example, the format of the scanning positional information may be Graphics Interchange Format (GIF), Portable Network Graphics (PNG), or Tagged Image File Format (TIFF).

Referring back to FIG. 1, the pathological image creation apparatus 40 includes, for example, a microscope, a microscope camera, and an information processing apparatus such as a personal computer (PC). When a doctor or an engineer observes a specimen 213 collected by ultrasound image-guided biopsy through the microscope, the pathological image creation apparatus 40 uses the microscope camera to photograph the specimen 213 to generate a pathological image. Examples of the pathological image include a DICOM format image and a JPEG format image. The pathological image may be an image other than images of the DICOM format and the JPEG format. For example, the format of the pathological image may be GIF, PNG, or TIFF.

The image processing apparatus 30 is an image storage server or a workstation, and processes mammography images generated by the mammography apparatus 10, ultrasound images generated by the ultrasound diagnosis apparatus 20, and pathological images generated by the pathological image creation apparatus 40. The image processing apparatus 30 is used to request pathological diagnosis to a pathologist.

Figure 5:
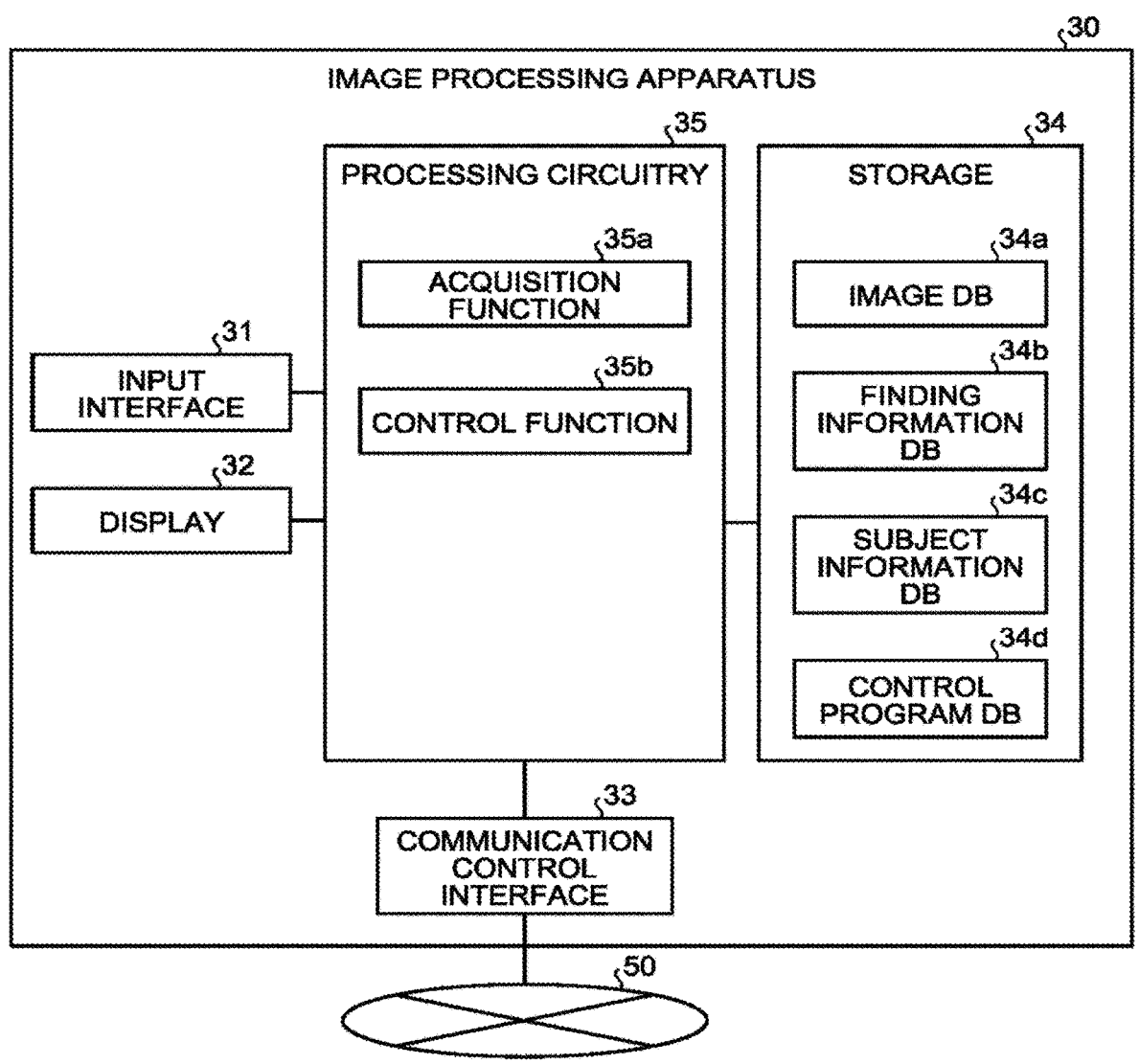
FIG. 5 is a diagram illustrating a configuration example of an image processing apparatus according to the first embodiment.

FIG. 5 is a diagram illustrating a configuration example of the image processing apparatus 30 according to the first embodiment. As illustrated in FIG. 5, the image processing apparatus 30 includes an input interface 31, a display 32, a communication control interface 33, a storage 34, and a processing circuitry 35.

The input interface 31 receives inputs of various kinds of operations and various kinds of information from the operator. Examples of the input interface 31 include a keyboard, a mouse, a button, a trackball, and a touch panel.

The display 32 displays a GUI for receiving various kinds of operations from the operator and various kinds of images. Examples of the display 32 include a liquid crystal display, a cathode ray tube (CRT) display, and a touch panel.

The communication control interface 33 controls communication performed between the image processing apparatus 30 and another apparatus through the network 50. Examples of the communication control interface 33 include a network card and a network adapter. The communication control interface 33 is connected to the network 50 through a LAN of Ethernet (registered trademark) to communicate with another apparatus. For example, the communication control interface 33 is connected to the network 50 through a wireless LAN to communicate with another apparatus in a wireless manner.

The storage 34 is a storage device configured to store therein an image database (DB) 34a, a finding information DB 34b, a subject information DB 34c, and a control program DB 34d for performing image processing and display processing. Data in various kinds of DBs stored in the storage 34 can be transferred to an external device through an interface (not shown).

For example, the image DB 34a stores therein mammography images obtained by taking images of breasts of subjects, which are generated by the mammography apparatus 10. For example, the image DB 34a stores therein ultrasound images and scanning positional information at the time of needling, which are generated by the ultrasound diagnosis apparatus 20. For example, the image DB 34a stores therein pathological images of specimens 213 obtained by needling, which are generated by the pathological image creation apparatus 40.

The finding information DB 34b stores therein finding information on mammography images of subjects. For example, the finding information DB 34b stores therein reading results of mammography images stored in the image DB 34a as finding information. More specifically, the finding information DB 34b stores therein mammography images in which regions of interest are set as reading results of the mammography images. For example, a region of interest in a mammography image is set by receiving the region of interest from the operator in the image processing apparatus 30 or by setting the result of detection by computer-aided diagnosis (CAD) as the region of interest.

The subject information DB 34c stores therein subject identifiers (IDs), names, ages, and consultation histories. The control program DB 34d stores therein computer programs corresponding to functions. The control program DB 34d is read by the processing circuitry 35. The processing circuitry 35 executes control programs read from the storage 34 to implement the functions corresponding to the computer programs.

The processing circuitry 35 controls the operation of the image processing apparatus 30. The processing circuitry 35 receives the setting of a region of interest in a mammography image from the operator. Then, the processing circuitry 35 causes the finding information DB 34b to store therein a mammography image, in which the region of interest is set, as finding information on the mammography image of the subject.

As illustrated in FIG. 5, the processing circuitry 35 executes an acquisition function 35a and a control function 35b. For example, processing functions to be executed by the acquisition function 35a and the control function 35b, which are components of the processing circuitry 35 illustrated in FIG. 5, are recorded in the storage 34 in the form of computer programs that can be executed by a computer. The processing circuitry 35 is a processor configured to implement the functions corresponding to the computer programs by reading the computer programs from the storage 34 and executing the read computer programs. In other words, the processing circuitry 35 that has read the computer programs has the functions illustrated in the processing circuitry 35 in FIG. 5. Details of the acquisition function 35a and the control function 35b are described later.

In the medical information processing system 100 described above, for example, a specimen obtained by biopsy is used for pathological diagnosis in breast cancer clinical practice. For example, specimens from ultrasound-guided biopsy are sent by a radiologist or a breast surgeon to a pathologist together with an ultrasound image and a pathological examination request. In general, the pathological examination request is formed of text information, and in some cases, a simple diagram simulating a breast is attached. The pathologist receives the specimen, the ultrasound image, and the pathological examination request, and performs a pathological diagnosis. For example, the pathologist grasps the whole picture from an ultrasound image of a subject. For a pathological diagnosis using a pathological image, the pathologist adds a finding from the ultrasound image to a finding from the pathological image in consideration of consistency between the ultrasound image and the pathological image, which enables a highly accurate diagnosis to be efficiently performed. Consequently, the pathologist can write and report a more reliable report to other clinicians.

Now, an example of a specimen and an ultrasound image sent to the pathologist is described with reference to FIG. 6. FIG. 6 is a diagram for describing the related art. FIG. 6 illustrates ultrasound images and pathological images of a lesion site found from the ultrasound images. For example, the pathological images illustrated in FIG. 6 are pathological images of a part of a specimen obtained by surgically cutting the entire lesion site found from an ultrasound image in which the observation target is a breast with surgery and cutting the lesion site into slices.

In the diagrams illustrated on the left side in FIG. 6, an ultrasound image is illustrated at the top, and a pathological image of a lesion site rendered in the ultrasound image is illustrated at the bottom. In the diagrams illustrated on the right side in FIG. 6, similarly to the diagrams illustrated on the left side in FIG. 6, an ultrasound image is illustrated at the top, and a pathological image of a lesion site rendered in the ultrasound image is illustrated at the bottom. In each of the diagrams illustrated in FIG. 6, a reference line L is illustrated. The reference lines L represent corresponding sites in the ultrasound image and the pathological image. As illustrated in FIG. 6, when the entire lesion site found from the ultrasound image is surgically cut with surgery, the shape of the lesion site rendered in the ultrasound image and the shape of a specimen in the pathological image are similar to each other, and hence the pathologist can easily associate the ultrasound image and the pathological image with each other.

In the case where a pathologist performs pathological diagnosis by using a pathological image, if a medical image obtained by taking an image of an observation target at a time point other than biopsy can be taken into consideration in addition to an ultrasound image at the biopsy, a more accurate diagnosis can be efficiently performed. In the medical information processing system 100, images obtained by taking images of an observation target at time points other than biopsy may be stored in some cases. For example, in the medical information processing system 100, mammography images obtained by taking images of an observation target before biopsy and mammography images obtained by taking images of an observation target after biopsy may be stored in some cases.

In view of the above, the image processing apparatus 30 according to the first embodiment executes correspondence information generation processing for setting an image obtained by taking an image of an observation target at a time point other than biopsy as a reference image and generating correspondence information in which an ultrasound image at biopsy and the reference image are associated with each other. Then, the image processing apparatus 30 provides the generated correspondence information to a pathologist, thereby assisting pathological diagnosis by the pathologist. The correspondence information generation processing executed by the image processing apparatus 30 is implemented by the acquisition function 35a and the control function 35b.

Specifically, the acquisition function 35a acquires an ultrasound image including an observation target and having additional information, positional information indicating the position of an ultrasound probe in a subject at the time of collection of the ultrasound image, and a reference image obtained by taking an image of a region including the observation target at a time point other than the time of the collection. The acquisition function 35a acquires an ultrasound image by determining information indicating a procedure for the observation target and information on operations for the ultrasound image as additional information. In one example, the acquisition function 35a determines the above-mentioned additional information based on subject information associated with an ID provided to the ultrasound image and information included in a tag of DICOM, and acquires an ultrasound image having the above-mentioned additional information.

For example, the acquisition function 35a acquires an ultrasound image at biopsy for collecting a specimen from an observation target, positional information indicating the position of an ultrasound probe 21 in a subject at the biopsy using the ultrasound image, and a reference image obtained by taking an image of the observation target at a time point other than the biopsy.

The control function 35b generates, based on the positional information, correspondence information in which the ultrasound image and the reference image are associated with each other, and causes the output unit to output the generated correspondence information. For example, the control function 35b generates correspondence information in which the ultrasound image at the biopsy and the reference image are associated with each other based on the positional information, and causes the display 32 to display the generated correspondence information. Details of the acquisition function 35a and the control function 35b are described below.

Figure 7:
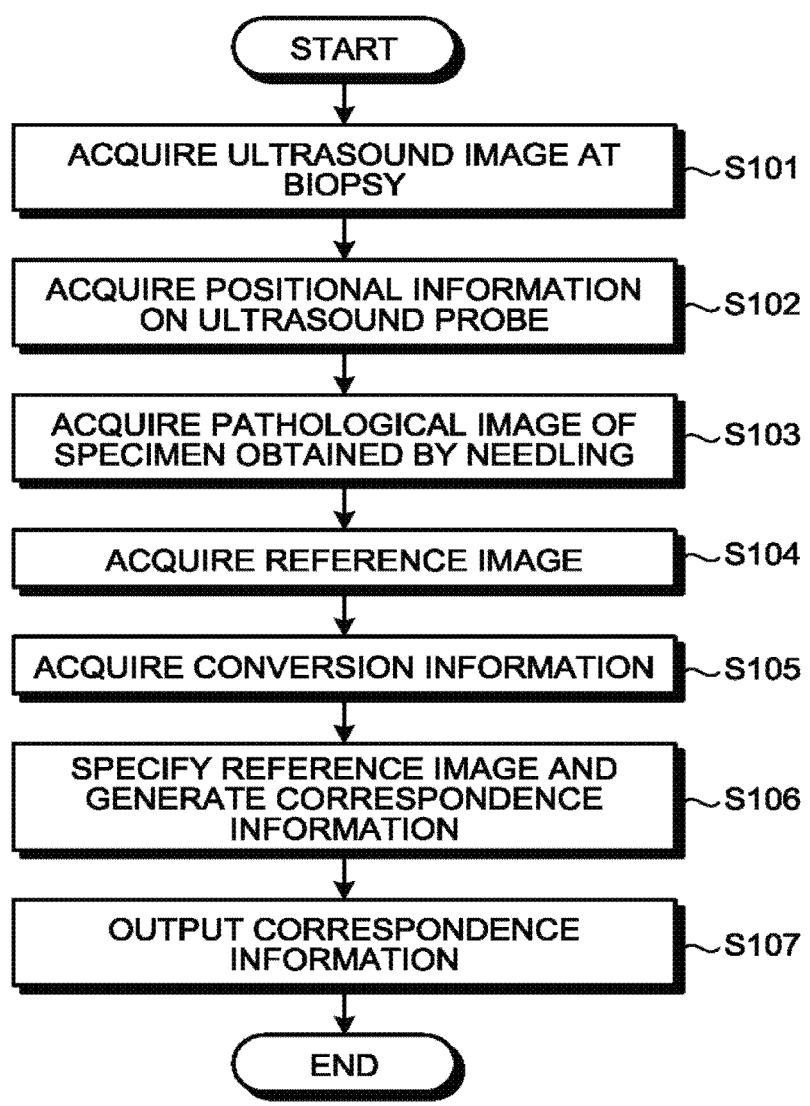
FIG. 7 is a flowchart illustrating a processing procedure of the image processing apparatus according to the first embodiment.

FIG. 7 is a flowchart illustrating a processing procedure of the image processing apparatus 30 according to the first embodiment. FIG. 8 to FIG. 11 are diagrams for describing the first embodiment. FIG. 7 illustrates a flowchart for describing the operation executed by the processing circuitry 35 in the image processing apparatus 30, and describes which of the steps in the flowchart each component corresponds to.

Step S101 to Step S104 are steps corresponding to the acquisition function 35a. The acquisition function 35a is implemented at the steps when the processing circuitry 35 invokes a predetermined computer program corresponding to the acquisition function 35a from the control program DB 34d of the storage 34 and executes the invoked computer program. At Step S101, the acquisition function 35a acquires an ultrasound image at biopsy.

Figure 8:
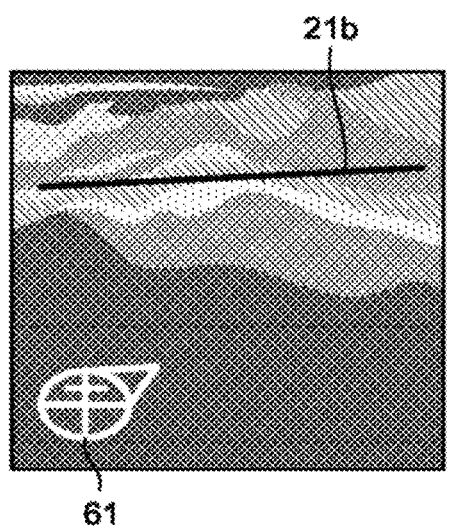
FIG. 8 is a diagram (1) for describing the first embodiment.

For example, when the acquisition function 35a receives a subject ID, an examination ID indicating examination at biopsy, and an apparatus ID indicating the ultrasound diagnosis apparatus 20 from an operator through the input interface 31, the acquisition function 35a acquires an ultrasound image matching the subject ID, the examination ID, and the apparatus ID from the image DB 34a. In one example, the acquisition function 35a acquires an ultrasound image as illustrated in FIG. 8 from the image DB 34a. As illustrated in FIG. 8, a puncture needle 21b is rendered in the ultrasound image. Scanning positional information 61, which is positional information indicating the position of the ultrasound probe 21 in the subject at biopsy, is superimposed and displayed on the ultrasound image.

At Step S102, the acquisition function 35a acquires positional information on the ultrasound probe 21. For example, the scanning positional information 61 is superimposed and displayed on the ultrasound image illustrated in FIG. 8. In such a case, the acquisition function 35a acquires the scanning positional information 61 from the ultrasound image to acquire the positional information on the ultrasound probe 21. In a case where the scanning positional information 61 is not superimposed and displayed on the ultrasound image, the acquisition function 35a acquires the scanning positional information from additional information on the ultrasound image to acquire the positional information on the ultrasound probe 21.

Figure 9:
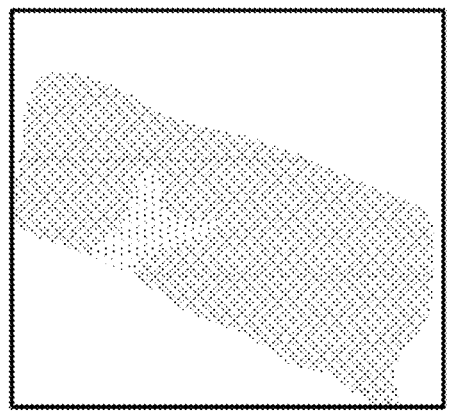
FIG. 9 is a diagram (2) for describing the first embodiment.

At Step S103, the acquisition function 35a acquires a pathological image of a specimen obtained by needling. For example, when the acquisition function 35a receives a subject ID, an examination ID indicating examination at specimen observation, and an apparatus ID indicating the pathological image creation apparatus 40 from the operator through the input interface 31, the acquisition function 35a acquires a pathological image matching the subject ID, the examination ID, and the apparatus ID from the image DB 34a. In one example, the acquisition function 35a acquires a pathological image of a specimen obtained by needling as illustrated in FIG. 9 from the image DB 34a. In the first embodiment, the acquisition function 35a may omit Step S103.

At Step S104, the acquisition function 35a acquires a reference image obtained by taking an image of the observation target at the time point other than biopsy. For example, when the acquisition function 35a receives a subject ID, an examination ID indicating examination where the image of the observation target is taken at the time point other than biopsy, and an apparatus ID indicating the mammography apparatus 10 from the operator through the input interface 31, the acquisition function 35a acquires a two-dimensional MLO image and a two-dimensional CC image matching the subject ID, the examination ID, and the apparatus ID from the image DB 34a as reference images.

Step S105 to Step S107 are steps corresponding to the control function 35b. The control function 35b is implemented at the steps when the processing circuitry 35 invokes a predetermined computer program corresponding to the control function 35b from the control program DB 34d of the storage 34 and executes the invoked computer program.

At Step S105, the control function 35b acquires conversion information in which a region of interest in the reference image is converted into a position on a schematic diagram of the breast. For example, the control function 35b acquires conversion information by using an echo scan guide function for converting and displaying the position of a finding registered on a mammography image into a body mark on ultrasound waves. For example, in the echo scan guide function, an intersection between an estimation line with which the position of a region of interest in a CC image is estimated on a body mark and an estimation line with which the position of the region of interest in an MLO image is estimated on the body mark is estimated as the position of the region of interest on the body mark.

At Step S106, the control function 35b specifies a reference image to generate correspondence information. In this case, the control function 35b uses positional information and conversion information to specify a reference image to be associated with the correspondence information. More specifically, when there are reference images, the control function 35b sets priorities to the reference images in ascending order of distance between the region of interest in the conversion information and the position of the ultrasound probe 21 in the scanning positional information.

Figure 10:
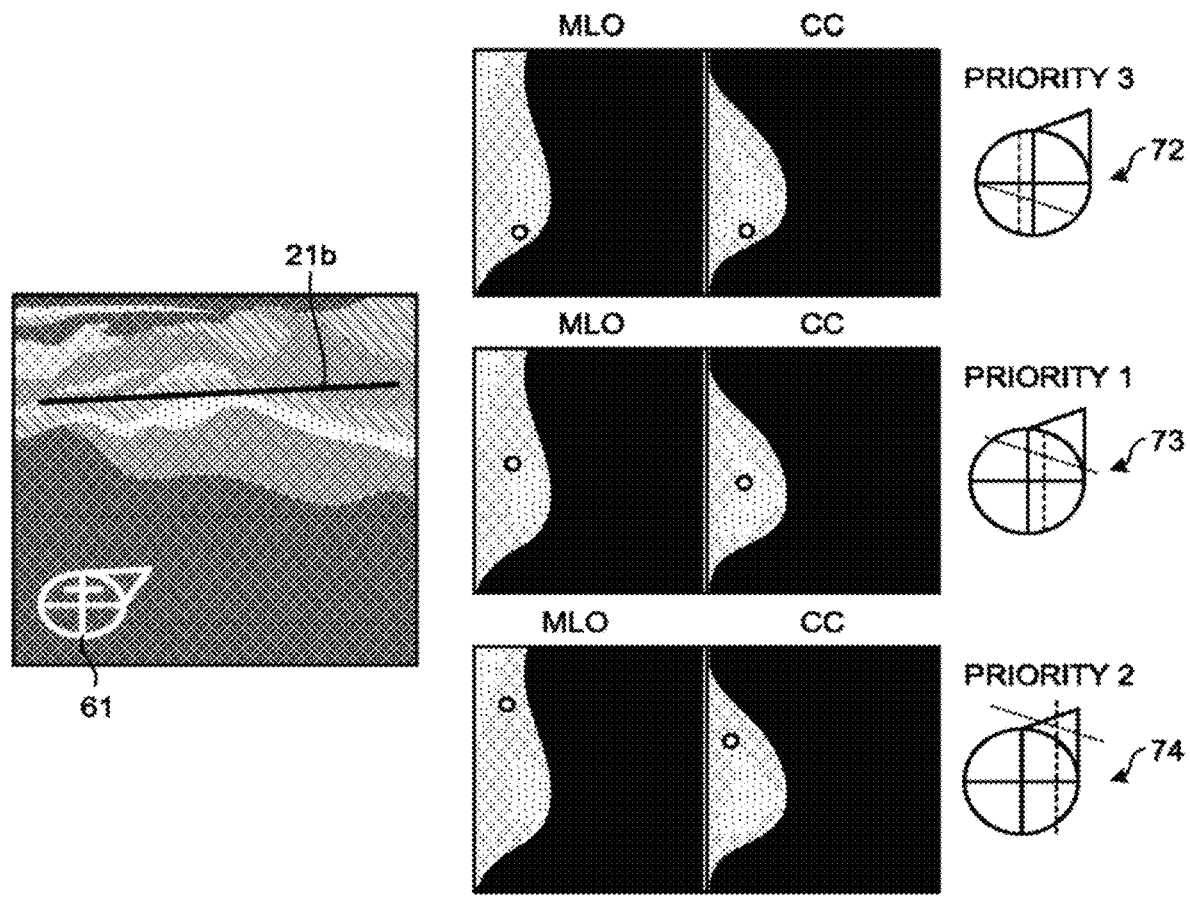
FIG. 10 is a diagram (3) for describing the first embodiment.

The left view in FIG. 10 illustrates an ultrasound image at biopsy. Scanning positional information 61 is superimposed on the ultrasound image. The scanning positional information 61 indicates that the position of the ultrasound probe 21 at biopsy corresponds to the middle between the region A and the region C on the schematic diagram. The right views in FIG. 10 illustrate three sets of mammography images, each of which has a CC image and an MLO image as a pair. In each of the mammography images, a region of interest indicated by a circle is set. In the right views in FIG. 10, conversion information 72 to 74 obtained by converting the region of interest into a position on a schematic diagram of the breast are illustrated for each set of mammography images. For example, the conversion information 72 indicates that the region of interest corresponds to the region B on the schematic diagram, the conversion information 73 indicates that the region of interest corresponds to the region C on the schematic diagram, and the conversion information 74 indicates that the region of interest corresponds to the region C' on the schematic diagram.

The control function 35b sets priorities in ascending order of distance between the region of interest in the conversion information 72 to 74 and the position of the ultrasound probe 21 in the scanning positional information 61. In one example, the position of the ultrasound probe 21 in the scanning positional information 61 corresponds to the middle between the region A and the region C on the schematic diagram, and hence the control function 35b sets the conversion information 73 in which the region of interest corresponds to the region C on the schematic diagram to "priority 1", which is the highest priority. The control function 35b sets the conversion information 74 in which the region of interest corresponds to the region C' on the schematic diagram to "priority 2", which is the second highest priority. Then, the control function 35b sets the conversion information 72 in which the region of interest corresponds to the region B on the schematic diagram to "priority 3", which is the third highest priority.

Figure 11:
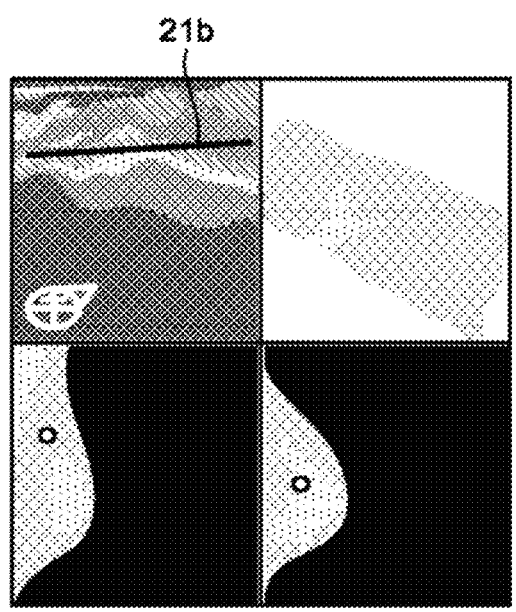
FIG. 11 is a diagram (4) for describing the first embodiment.

Then, the control function 35b associates reference images with correspondence information in the order of priority. For example, the control function 35b generates correspondence information in which the ultrasound image at biopsy including scanning positional information, which is acquired at Step S101, a pathological image generated after the biopsy based on a specimen obtained by the biopsy, which is acquired at Step S103, and mammography images (CC image and MLO image) having priority 1 are associated with one another. More specifically, as illustrated in FIG. 11, the control function 35b generates correspondence information in which an ultrasound image at biopsy including scanning positional information is arranged on the upper left side, a pathological image is arranged on the upper right side, an MLO image specified as a reference image is arranged on the lower left side, and a CC image specified as a reference image is arranged on the lower right side. In the case where Step S103 is omitted and no pathological image has been acquired, the control function 35b generates correspondence information excluding the pathological image.

At Step S107, the control function 35b outputs the correspondence information. For example, the control function 35b causes the display 32 to display the correspondence information illustrated in FIG. 11. In this manner, the control function 35b associates reference images with correspondence information in the order of priority and causes the display 32 to display the correspondence information.

As described above, in the first embodiment, the image processing apparatus 30 acquires a reference image obtained by taking an image of an observation target at a time point other than biopsy. Then, the image processing apparatus 30 causes the display 32 to display the reference image associated as correspondence information. Consequently, according to the first embodiment, for example, for a pathological diagnosis using a pathological image, a pathologist can add findings from ultrasound images and reference images to a finding from the pathological image, which enables a more accurate diagnosis to be efficiently performed. As a result, the pathologist can write and report a more reliable report to other clinicians.

In the first embodiment, the control function 35b may cause the display 32 to display correspondence information while switching reference information in descending order of priority. In such a case, for example, the control function 35b generates correspondence information in which an ultrasound image at biopsy having scanning positional information superimposed thereon, a pathological image of a specimen obtained by the biopsy, and a reference image having the highest priority are associated with one another, and causes the display 32 to display the correspondence information. Then, when the control function 35b receives an instruction to switch the reference image from the operator through the input interface 31, the control function 35b changes the reference image to an image having the second highest priority without changing an ultrasound image at biopsy having scanning positional information superimposed thereon and a pathological image of a specimen obtained by the biopsy. In the case where a reference image having the lowest priority is displayed when an instruction to switch the reference image is received from the operator, the control function 35b may change the reference image to a reference image having the highest priority again and switch reference information in descending order of priority, or may change the reference image to a reference image having the second highest priority, switch reference information in ascending order of priority, and when the reference image has been switched to a reference image having the highest priority, switch the reference information in descending order of priority again.

In the above-mentioned embodiment, the case where the reference image is a two-dimensional mammography image has been described, but the embodiment is not limited thereto. For example, an ultrasound image obtained by taking an image of an observation target at the time point other than biopsy may be used as a reference image.

Modification of First Embodiment

Figure 12A:
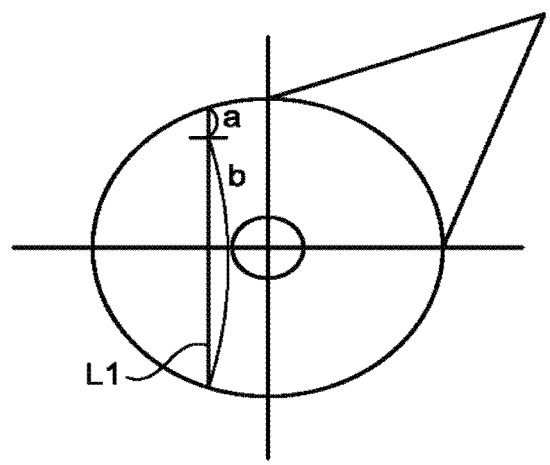
FIG. 12A is a diagram (1) for describing a modification of the first embodiment.
Figure 12B:
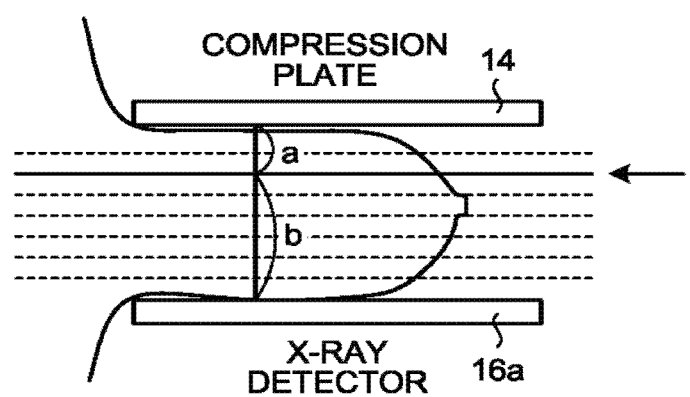
FIG. 12B is a diagram (2) for describing the modification of the first embodiment.

In the above-mentioned embodiment, the case where a two-dimensional mammography image as a reference image is associated with correspondence information has been described, but the embodiments are not limited thereto. For example, a tomosynthesis image may be associated with correspondence information as a reference image. When a reference image is a three-dimensional image, the control function 35*b* associates an image of the cross section corresponding to the position of the ultrasound probe 21 based on scanning positional information with the correspondence information. FIG. 12A and FIG. 12B are diagrams for describing a modification of the first embodiment.

FIG. 12A illustrates scanning positional information indicating the position of an ultrasound probe 21 in a subject at biopsy. In FIG. 12A, a straight probe mark is indicated on a schematic diagram of the left breast. For example, when the control function 35*b* acquires the scanning positional information illustrated in FIG. 12A, the control function 35*b* determines (a:b) as the ratio of position of the probe mark to L1.

FIG. 12B illustrates the case where a breast of a subject is fixed under pressure between a compression plate 14 and an X-ray detector 16*a*. Cross sections of a tomosynthesis image generated when tomosynthesis imaging is performed in this state are illustrated by broken lines. As illustrated in FIG. 12B, the control function 35*b* determines a cross section in which the ratio of an intersection between a straight line connecting the compression plate 14 and the X-ray detector 16*a* with shortest distance and the cross section of the tomosynthesis image is (a:b). In the example illustrated in FIG. 12B, the control function 35*b* determines the second cross section from the compression plate 14 as a cross section having the ratio of (a:b). Then, the control function 35*b* determines that the determined cross section is a surface to be scanned by the ultrasound probe 21, and associates a tomosynthesis image of the cross section with correspondence information as a reference image.

As described above, in the modification of the first embodiment, the image processing apparatus 30 acquires a three-dimensional image obtained by taking an image of an observation target at the time point other than biopsy as a reference image. Then, the image processing apparatus 30 causes the display 32 to display the reference image associated with correspondence information. Consequently, according to the modification of the first embodiment, for example, a pathologist can easily grasp the correspondence relation between an ultrasound image at biopsy and a pathological image of a specimen obtained by the biopsy. In addition, for a pathological diagnosis using a pathological image, the pathologist can add findings from the ultrasound image and a three-dimensional image to a finding from the pathological image, which enables a more accurate diagnosis to be efficiently performed. As a result, the pathologist can write and report a more reliable report to other clinicians.

The control function 35*b* according to the modification of the first embodiment may associate a two-dimensional image and a three-dimensional image with correspondence information as reference images. In such a case, the control function 35*b* may receive the selection of an image to be associated as a reference image from the operator through the input interface 31. For example, each time the operator clicks a mouse, the image to be associated with correspondence information as a reference image may be switched to a two-dimensional image, a three-dimensional image, and a two-dimensional image and a three-dimensional image in a predetermined order.

In the above-mentioned embodiment, a tomosynthesis image and a three-dimensional ultrasound image have been described as an example where a reference image is a three-dimensional image, but the embodiments are not limited thereto. For example, an image obtained by taking an image of an observation target at a time point other than biopsy by an X-ray computed tomography (CT) apparatus or a magnetic resonance imaging (MRI) apparatus may be used as a reference image.

Second Embodiment

In the first embodiment, the case where an image in which the position of scanning by the ultrasound probe 21 and a region of interest are close to each other is associated as a reference image has been described. In a second embodiment, the case where an image of a cross section corresponding to the position of a puncture needle at biopsy is associated with correspondence information as a reference image is described.

The entire configuration of a medical information processing system 100 according to the second embodiment is the same as a configuration example of the medical information processing system 100 illustrated in FIG. 1 except that a part of functions is added to the control function 35*b* executed by the processing circuitry 35 included in the image processing apparatus 30. Thus, detailed descriptions of units having the same functions as in the configuration example of the medical information processing system 100 illustrated in FIG. 1 are omitted.

For example, the control function 35*b* according to the second embodiment calculates a distance from the body surface to a needling position in an ultrasound image at biopsy, and specifies a corresponding cross-section in a three-dimensional image based on the calculated distance information. In the second embodiment, the case where a three-dimensional ultrasound image obtained by taking an image of an observation target at the time point other than biopsy is associated with correspondence information as a reference image is described.

Figure 13:
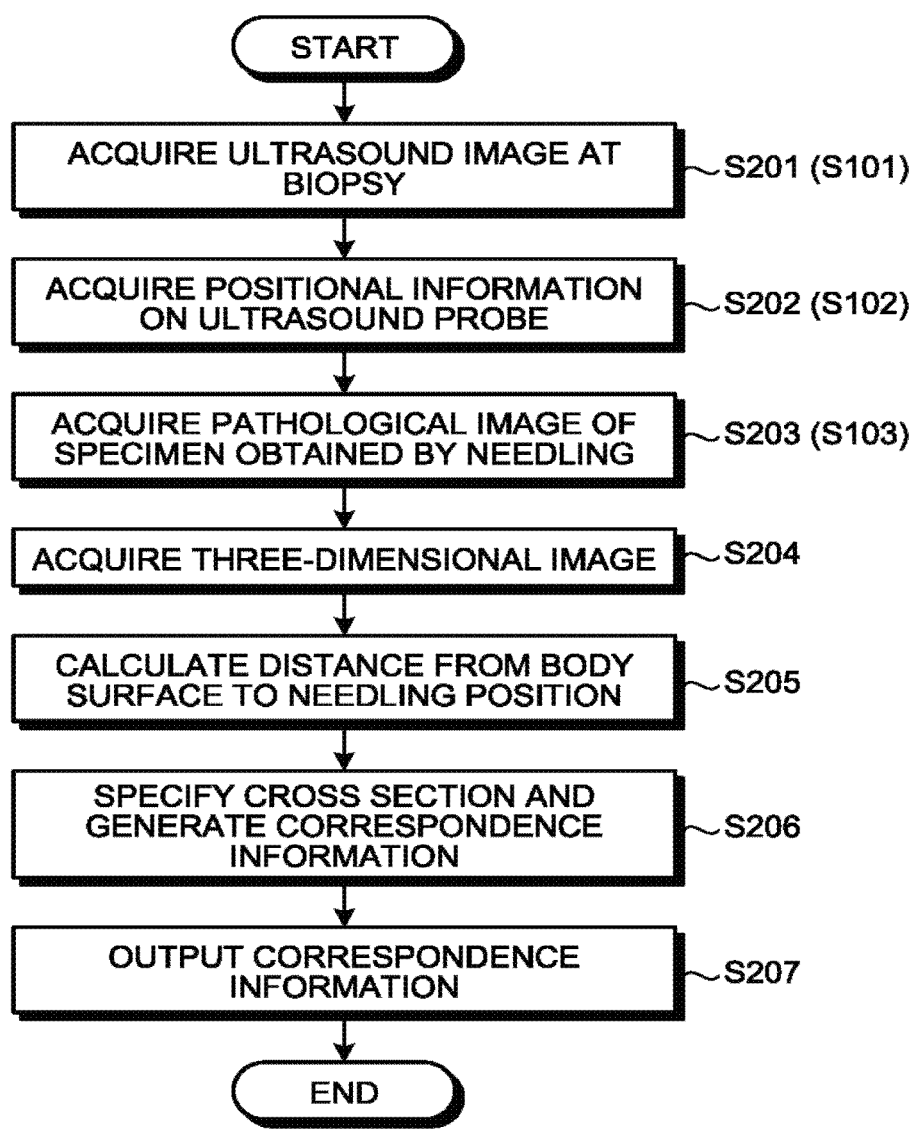
FIG. 13 is a flowchart illustrating a processing procedure of an image processing apparatus according to a second embodiment.
Figure 14A:
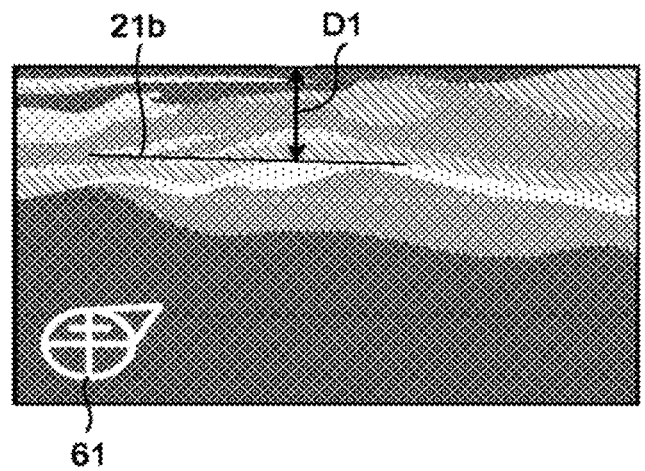
FIG. 14A is a diagram (1) for describing the second embodiment.
Figure 14B:
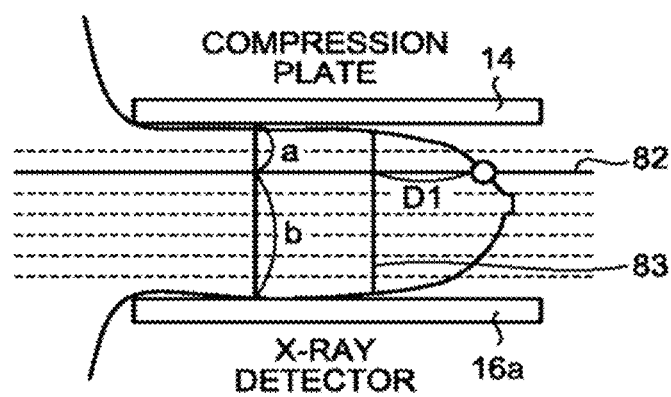
FIG. 14B is a diagram (2) for describing the second embodiment.
Figure 14C:
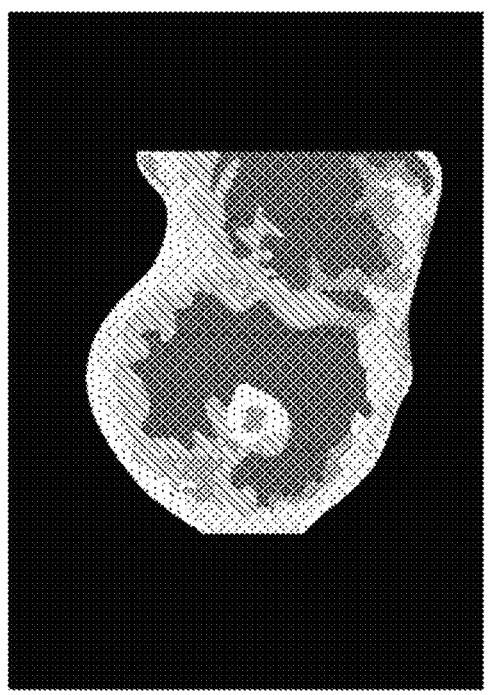
FIG. 14C is a diagram (3) for describing the second embodiment.
Figure 15:
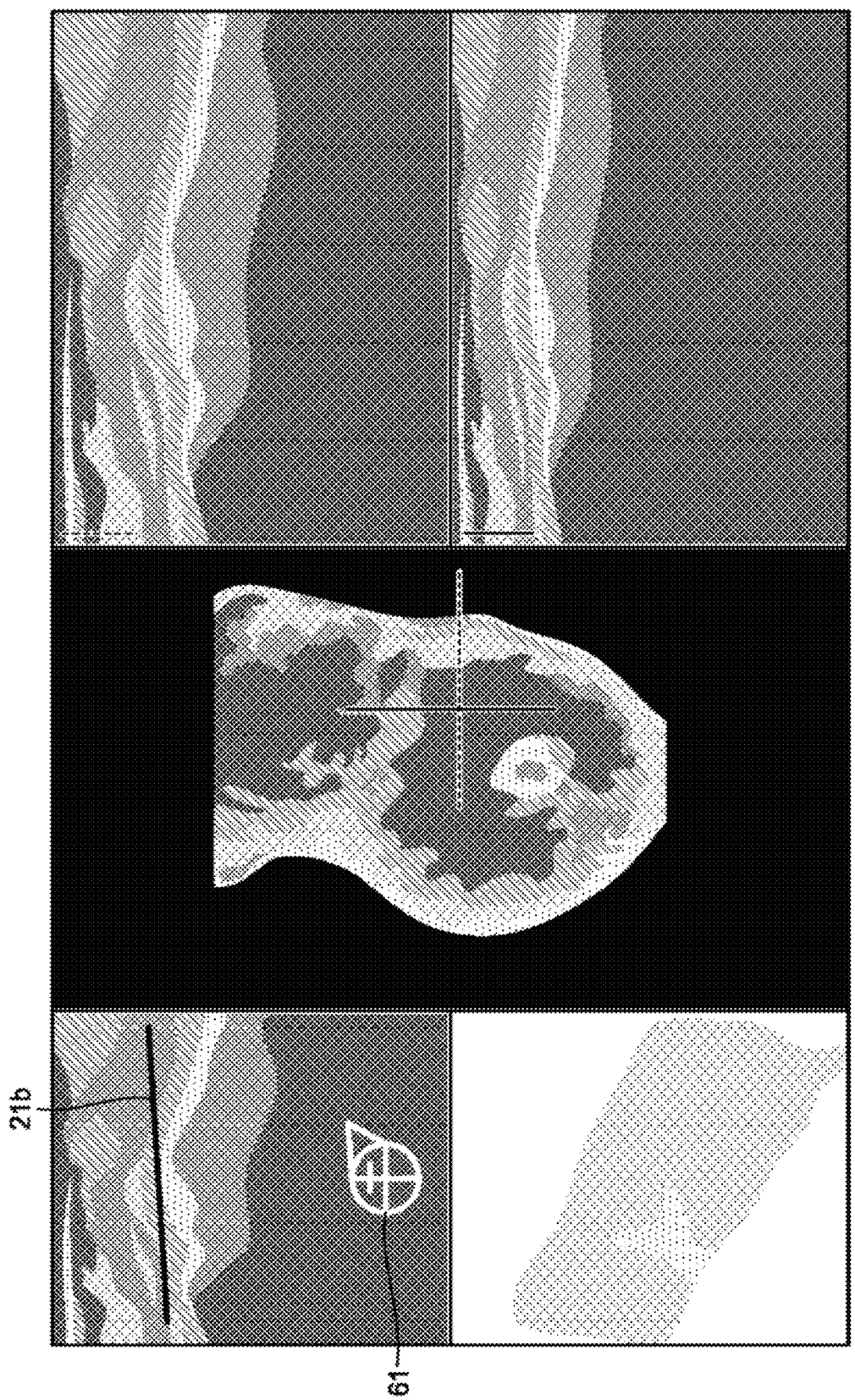
FIG. 15 is a diagram (4) for describing the second embodiment.

FIG. 13 is a flowchart illustrating a processing procedure of the image processing apparatus 30 according to the second embodiment. FIG. 14A to FIG. 15 are diagrams for describing the second embodiment. FIG. 13 illustrates a flowchart for describing the operation executed by the processing circuitry 35 in the image processing apparatus 30, and describes which of the steps in the flowchart each component corresponds to.

Step S201 to Step S204 are steps corresponding to the acquisition function 35*a*. The acquisition function 35*a* is implemented at the steps when the processing circuitry 35 invokes a predetermined computer program corresponding to the acquisition function 35*a* from the control program DB 34*d* of the storage 34 and executes the invoked computer program. Step S201 to Step S203 are similar to the processing at Step S101 to Step S103 illustrated in FIG. 7, and hence detailed descriptions thereof are omitted. In the second embodiment, the acquisition function 35*a* may omit Step S203.

At Step S204, the acquisition function 35*a* acquires a three-dimensional image obtained by taking an image of an observation target at the time point other than biopsy. For example, when the acquisition function 35*a* receives a subject ID, an examination ID indicating examination where the image of the observation target is taken at the time point other than biopsy, and an apparatus ID indicating the ultrasound diagnosis apparatus 20 capable of taking a three-dimensional ultrasound image from the operator through the input interface 31, the acquisition function 35*a* acquires a three-dimensional ultrasound image matching the subject ID, the examination ID, and the apparatus ID from the image DB 34*a*.

Step S205 to Step S207 are steps corresponding to the control function 35b. The control function 35b is implemented at the steps when the processing circuitry 35 invokes a predetermined computer program corresponding to the control function 35b from the control program DB 34d of the storage 34 and executes the invoked computer program.

At Step S205, the control function 35b calculates a distance from the body surface to a needling position in an ultrasound image at biopsy. FIG. 14A illustrates an ultrasound image at biopsy. In the ultrasound image, a puncture needle 21b is rendered. As illustrated in FIG. 14A, the control function 35b calculates a distance D1 from the body surface to a needling position in the ultrasound image.

At Step S206, the control function 35b specifies a cross section to generate correspondence information. For example, the control function 35b specifies a corresponding cross section in a three-dimensional image based on the distance information calculated at Step S205. In the ultrasound image acquired at Step S201, scanning positional information 61 is superimposed as illustrated in FIG. 14A. The control function 35b determines from the scanning positional information 61 a cross section corresponding to the surface to be scanned by the ultrasound probe 21 in the same manner as in the processing described above with reference to FIG. 12A and FIG. 12B. For example, as illustrated in FIG. 14B, the control function 35b determines a cross section 82 corresponding to a surface to be scanned by the ultrasound probe 21 based on the scanning positional information 61. Then, the control function 35b specifies a cross section 83 at a position at a distance D1 in the determined cross section 82 from the body surface, which is calculated in the dorsoventral direction of the subject. In one example, the control function 35b specifies, as the cross section 83, an ultrasound image illustrated in FIG. 14C as a reference image based on a three-dimensional ultrasound image.

Then, the control function 35b associates the reference image with correspondence information. For example, the control function 35b generates correspondence information in which the ultrasound image at biopsy including the scanning positional information, which is acquired at Step S201, the pathological image generated after the biopsy based on a specimen obtained by the biopsy, which is acquired at Step S203, and the ultrasound image corresponding to cross section 83, which is illustrated in FIG. 14C, are associated with one another. More specifically, as illustrated in FIG. 15, the control function 35b arranges an ultrasound image at biopsy including scanning positional information at the top on the left side, arranges a pathological image at the bottom on the left side, and arranges an ultrasound image of the cross section 83 at the center as a reference image. In addition, as illustrated in FIG. 15, the control function 35b arranges an ultrasound image of a cross section indicated by the broken line in the ultrasound image of the cross section 83 at the top on the right side, and arranges an ultrasound image of a cross section indicated by the solid line in the ultrasound image of the cross section 83 at the bottom on the right side.

At Step S207, the control function 35b outputs the correspondence information generated at Step S206. For example, the control function 35b causes the display 32 to display correspondence information illustrated in FIG. 15.

As described above, in the second embodiment, when the reference image is a three-dimensional image, the image processing apparatus 30 associates an image of the cross section corresponding to the position of the ultrasound probe 21 based on the scanning positional information with the correspondence information. As a result, according to the second embodiment, for example, for a pathological diagnosis using a pathological image, a pathologist can add findings from an ultrasound image and a reference image of a cross section corresponding to the distance from the body surface to a needling position to a finding from the pathological image, which enables a more accurate diagnosis to be efficiently performed. Consequently, the pathologist can write and report a more reliable report to other clinicians.

Third Embodiment

In the above-mentioned embodiments, the case where correspondence information in which an ultrasound image and a reference image are associated with each other is generated has been described. A pathological image obtained from a specimen collected by the puncture needle 21b is different from a pathological image obtained from a specimen obtained by surgically cutting the entire lesion site with surgery, and is a part of a lesion site rendered on an ultrasound image. Thus, it may be difficult for a pathologist to grasp a correspondence relation between an ultrasound image and a pathological image in a pathological diagnosis. In view of the above, in a third embodiment, the case of generating correspondence information further associated with a pathological image is described.

The entire configuration of a medical information processing system 100 according to the third embodiment is the same as in a configuration example of the medical information processing system 100 illustrated in FIG. 1 except that a part of functions is added to the control function 35b executed by the processing circuitry 35 included in the image processing apparatus 30. Thus, detailed descriptions of units having the same functions as in a configuration example of the medical information processing system 100 illustrated in FIG. 1 are omitted.

For example, the acquisition function 35a according to the third embodiment further acquires a pathological image that is generated after biopsy based on a specimen obtained by biopsy. Then, the control function 35b according to the third embodiment causes the display 32 to display the pathological image further associated with correspondence information in which an ultrasound image at biopsy and a reference image are associated with each other.

Figure 16:
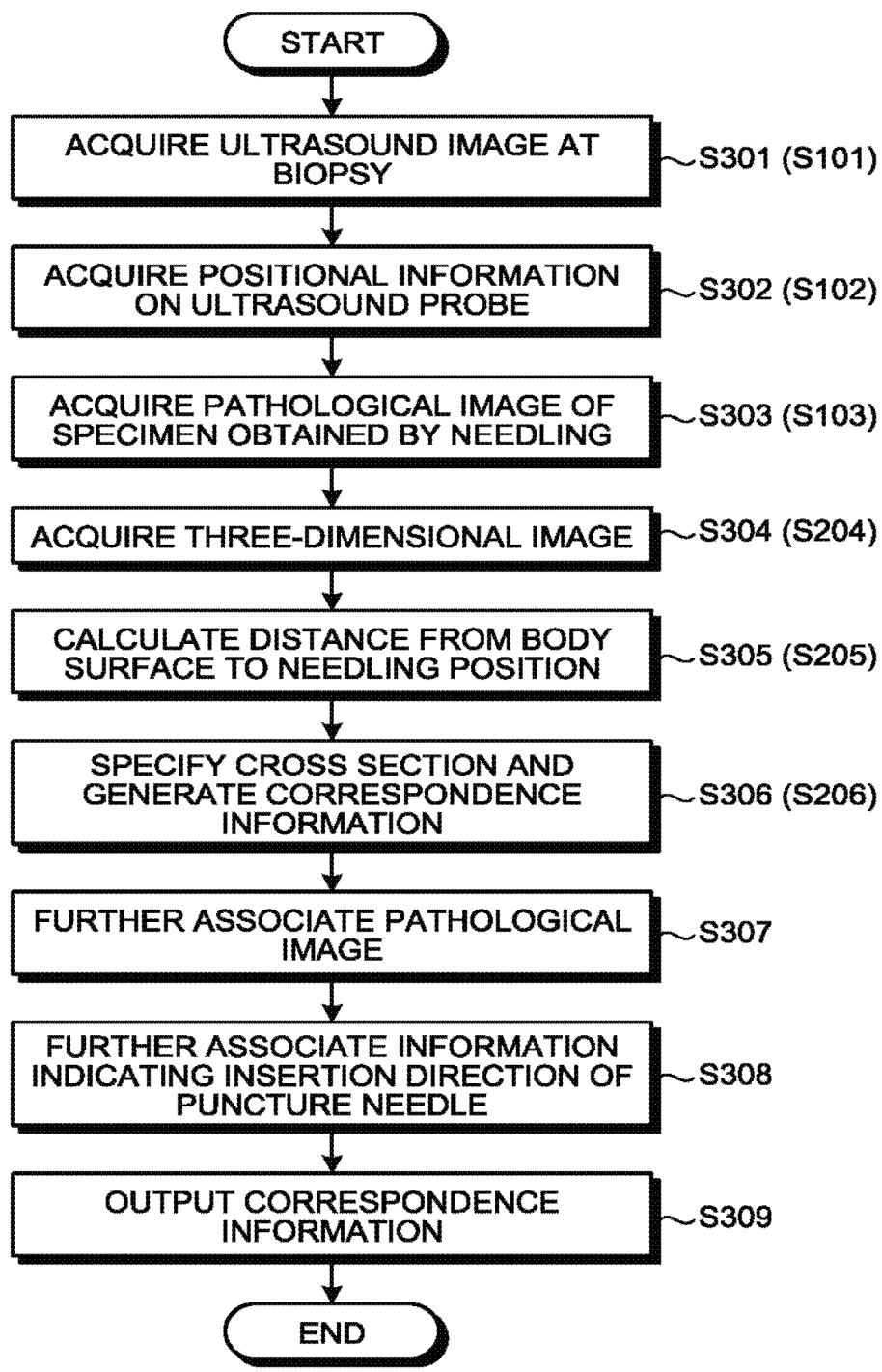
FIG. 16 is a flowchart illustrating a processing procedure of an image processing apparatus according to a third embodiment.
Figure 17:
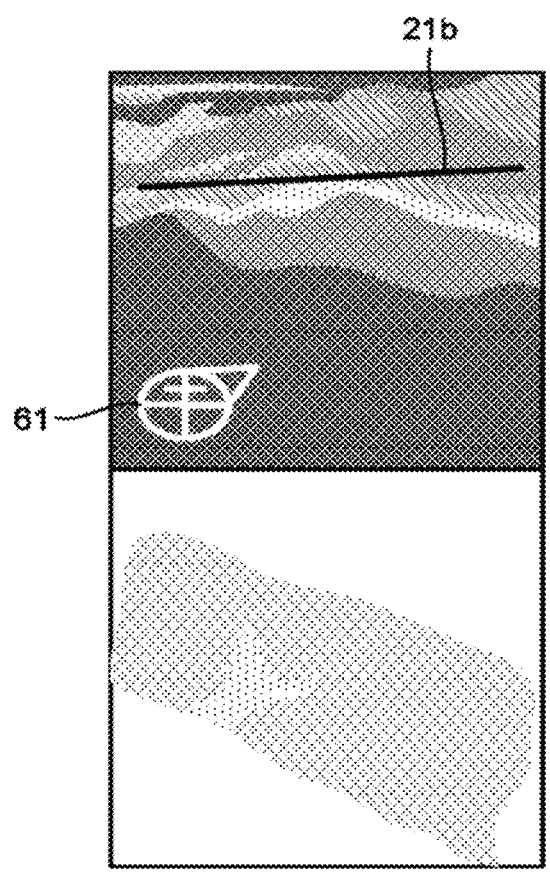
FIG. 17 is a diagram (1) for describing the third embodiment.
Figure 18:
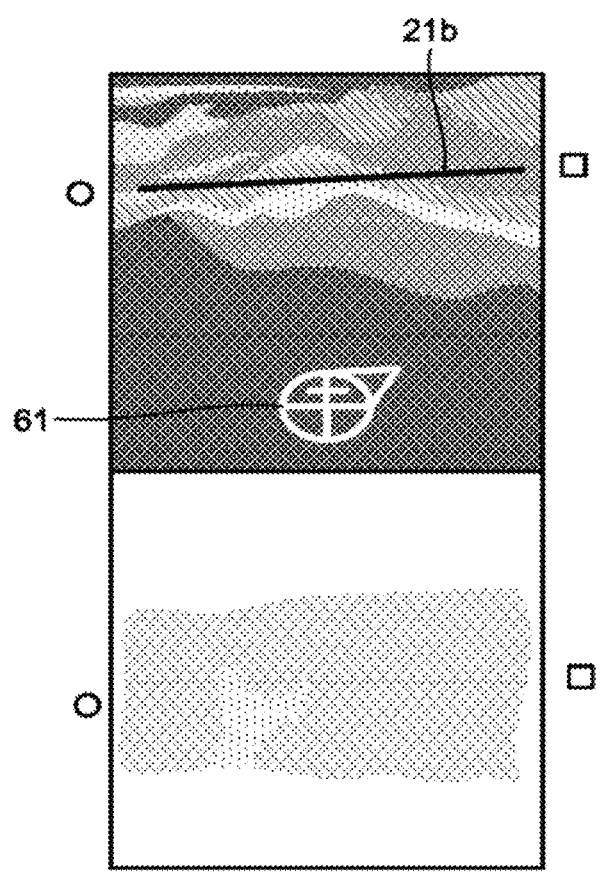
FIG. 18 is a diagram (2) for describing the third embodiment.
Figure 19:
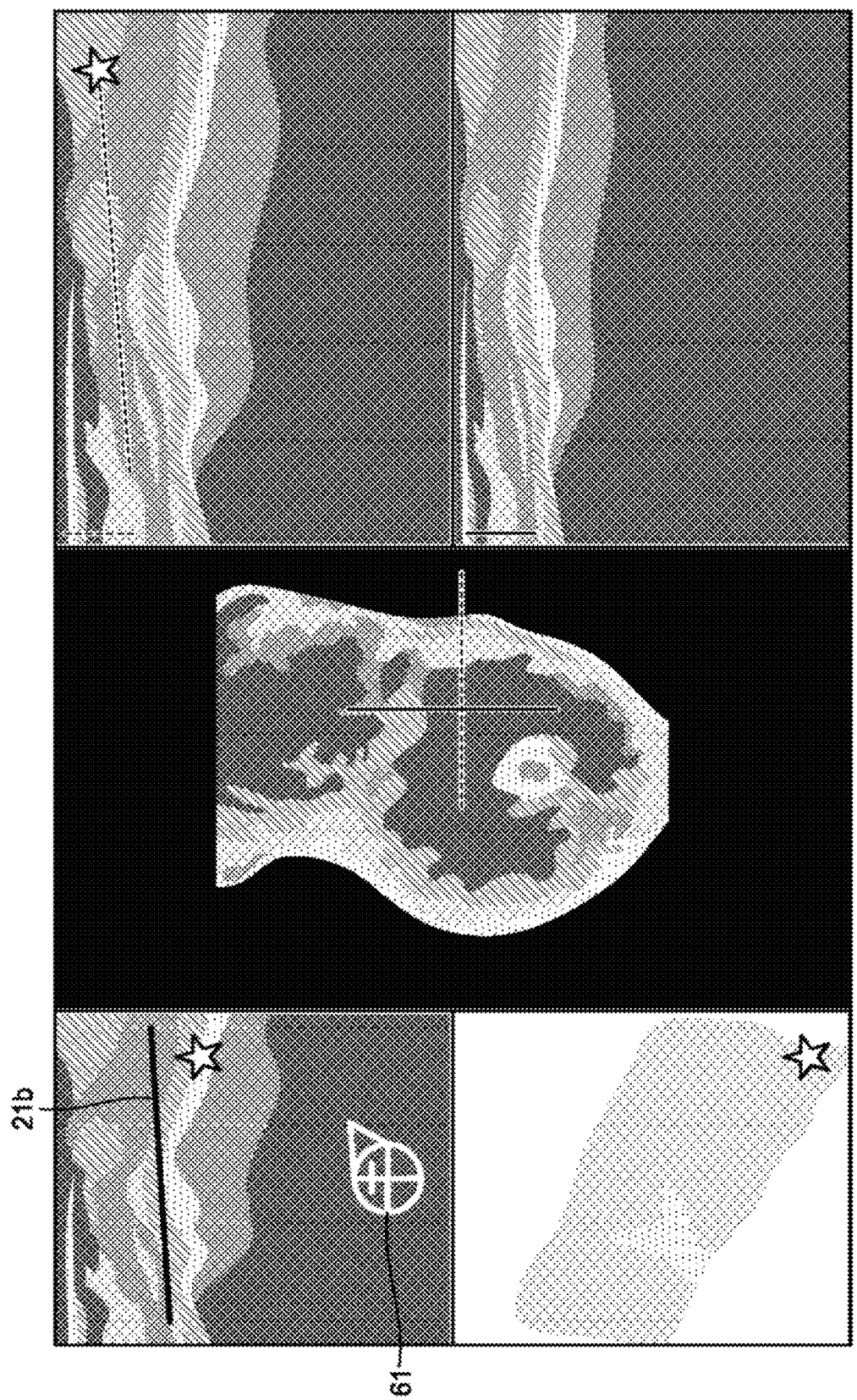
FIG. 19 is a diagram (3) for describing the third embodiment.

FIG. 16 is a flowchart illustrating a processing procedure of the image processing apparatus 30 according to the third embodiment. FIG. 17 to FIG. 19 are diagrams for describing the third embodiment. FIG. 16 illustrates a flowchart for describing the operation executed by the processing circuitry 35 in the image processing apparatus 30, and describes which of the steps in the flowchart each component corresponds to. Referring to FIG. 16, the case where the control function 35b further associates a pathological image with the correspondence information described in the second embodiment is described.

Step S301 to Step S304 are steps corresponding to the acquisition function 35a. The acquisition function 35a is implemented at the steps when the processing circuitry 35 invokes a predetermined computer program corresponding to the acquisition function 35a from the control program DB 34d of the storage 34 and executes the invoked computer program. Step S301 to Step S304 are the same as the processing at Step S201 to Step S204 illustrated in FIG. 13, and hence detailed descriptions thereof are omitted. In the third embodiment, the acquisition function 35a does not omit but executes Step S303.

Step S305 to Step S309 are steps corresponding to the control function 35b. The control function 35b is implemented at the steps when the processing circuitry 35 invokes a predetermined computer program corresponding to the control function 35b from the control program DB 34d of the storage 34 and executes the invoked computer program. Step S305 and Step S306 are the same as the processing at Step S205 and Step S206 illustrated in FIG. 13, and hence detailed descriptions thereof are omitted.

At Step S307, the control function 35b further associates a pathological image. For example, as illustrated in FIG. 17, the control function 35b associates the pathological image acquired at Step S303 with the ultrasound image acquired at Step S301. The upper view in FIG. 17 is the ultrasound image illustrated in FIG. 8, and includes scanning positional information 61. The lower view in FIG. 17 is the pathological image illustrated in FIG. 9. In other words, the control function 35b generates correspondence information in which the ultrasound image illustrated in FIG. 8 and the pathological image illustrated in FIG. 9 are associated with each other. For the sake of description, FIG. 17 omits the illustration of reference images, and illustrates the ultrasound image including the scanning positional information 61 and the pathological image. In this manner, the control function 35b further associates the pathological image acquired at Step S303 with the correspondence information generated at Step S306.

At Step S308, the control function 35b further associates information indicating the insertion direction of the puncture needle 21b. Similarly to FIG. 17, the upper view in FIG. 18 is an ultrasound image, and the lower view in FIG. 18 is a pathological image. For example, the control function 35b sets information indicating the insertion direction of the puncture needle 21b at biopsy, for example, in the ultrasound image illustrated in the upper view in FIG. 18. In the following, information indicating the insertion direction of the puncture needle 21b at biopsy is referred to also as "puncture needle information".

More specifically, the control function 35b receives information indicating the insertion direction of the puncture needle 21b at biopsy on the ultrasound image from the operator through the input interface 31. The control function 35b receives, from the operator, the setting of at least one of the needle tip side and the needle insertion side of the puncture needle 21b at biopsy on the ultrasound image. In the example illustrated in the upper view in FIG. 18, the control function 35b receives the setting of the needle tip side and the needle insertion side. Then, the control function 35b associates the puncture needle information received from the operator on the ultrasound image. In the upper view in FIG. 18, the needle tip side is indicated by a circle, and the needle insertion side is indicated by a rectangle.

The control function 35b receives information indicating the insertion direction of the puncture needle 21b at biopsy on the pathological image from the operator through the input interface 31. The control function 35b receives, from the operator, the setting of at least one of the needle tip side and the needle insertion side of the puncture needle 21b at biopsy on the pathological image. In the example illustrated in the lower view in FIG. 18, the control function 35b receives the setting of the needle tip side and the needle insertion side. Then, the control function 35b associates the puncture needle information received from the operator on the pathological image. In the lower view in FIG. 18, the needle tip side is indicated by a circle, and the needle insertion side is indicated by a rectangle.

Then, the control function 35b rotates or translates at least one of the ultrasound image and the pathological image such that the orientation of the puncture needle information set on the ultrasound image and the orientation of the puncture needle information set on the pathological image substantially match with each other. The pathological image illustrated in the lower view in FIG. 18 is obtained by rotationally moving the pathological image illustrated in the lower view in FIG. 17.

At Step S309, the control function 35b outputs the correspondence information. For example, the control function 35b causes the display 32 to display the correspondence information further associated with the puncture needle information at Step S308.

For example, the control function 35b causes the display 32 to display the correspondence information illustrated in FIG. 19. In FIG. 19, the control function 35b arranges an ultrasound image at biopsy including scanning positional information 61 at the top on the left side, arranges a pathological image at the bottom on the left side, arranges an ultrasound image of a cross section 83 at the center as a reference image, arranges a cross section indicated by the broken line in the ultrasound image of the cross section 83 at the top on the right side, and arranges a cross section indicated by the solid line in the ultrasound image of the cross section 83 at the bottom on the right side. In addition, for example, the control function 35b superimposes, as puncture needle information, a star indicating the tip side of the puncture needle 21b on the ultrasound image at the biopsy including the scanning positional information arranged at the top on the left side and on the pathological image arranged at the bottom on the left side. The control function 35b displays the puncture needle 21b in a pseudo manner on the ultrasound image at the top on the right side obtained by taking an image of the observation target at a time point other than the biopsy, and superimposes a star indicating the tip side of a pseudo puncture needle as puncture needle information. In this manner, the control function 35b further associates a pathological image and information indicating the insertion direction of the puncture needle 21b at the biopsy with the correspondence information described in the second embodiment, and causes the display 32 to display the correspondence information.

As described above, in the third embodiment, the image processing apparatus 30 further associates a pathological image with correspondence information in which an ultrasound image at biopsy and a reference image are associated with each other, and causes the display 32 to display the correspondence information. In this manner, according to the third embodiment, for example, a pathologist can easily grasp the correspondence relation between an ultrasound image at biopsy and a pathological image of a specimen obtained by the biopsy. As a result, for a pathological diagnosis using a pathological image, the pathologist can add a finding from an ultrasound image and a finding from a reference image to a finding from the pathological image in consideration of consistency between the ultrasound image and the pathological image, which enables a more accurate diagnosis to be efficiently performed. In addition, a pathologist can write and report a more reliable report to other clinicians.

In the above-mentioned third embodiment, the case where a pathological image is further associated with the correspondence information described in the second embodiment has been described, but the embodiments are not limited thereto. For example, a pathological image may be further associated with the correspondence information described in the first embodiment. In such a case, the control function 35*b* executes the processing of Step S307 and Step S308 illustrated in FIG. 16 after the end of Step S106 illustrated in FIG. 7, and then executes the processing of Step S107.

In the above-mentioned third embodiment, the control function 35*b* further associates a pathological image of a specimen obtained by biopsy and puncture needle information with correspondence information in which an ultrasound image at the biopsy and a reference image are associated with each other, and causes the display 32 to display the correspondence information, but the embodiments are not limited thereto. For example, the control function 35*b* may receive an instruction to turn on and off the display of the puncture needle information from an operator through the input interface 31.

Modification of Third Embodiment

In the above-mentioned third embodiment, a pathological image is further associated with correspondence information in which an ultrasound image at biopsy and a reference image are associated with each other, but the embodiments are not limited thereto. For example, the control function 35*b* may generate correspondence information in which an ultrasound image at biopsy, scanning positional information indicating the position of the ultrasound probe 21 in a subject at the biopsy using the ultrasound image, and a pathological image generated after the biopsy based on a specimen obtained by the biopsy are associated with one another.

Figure 20:
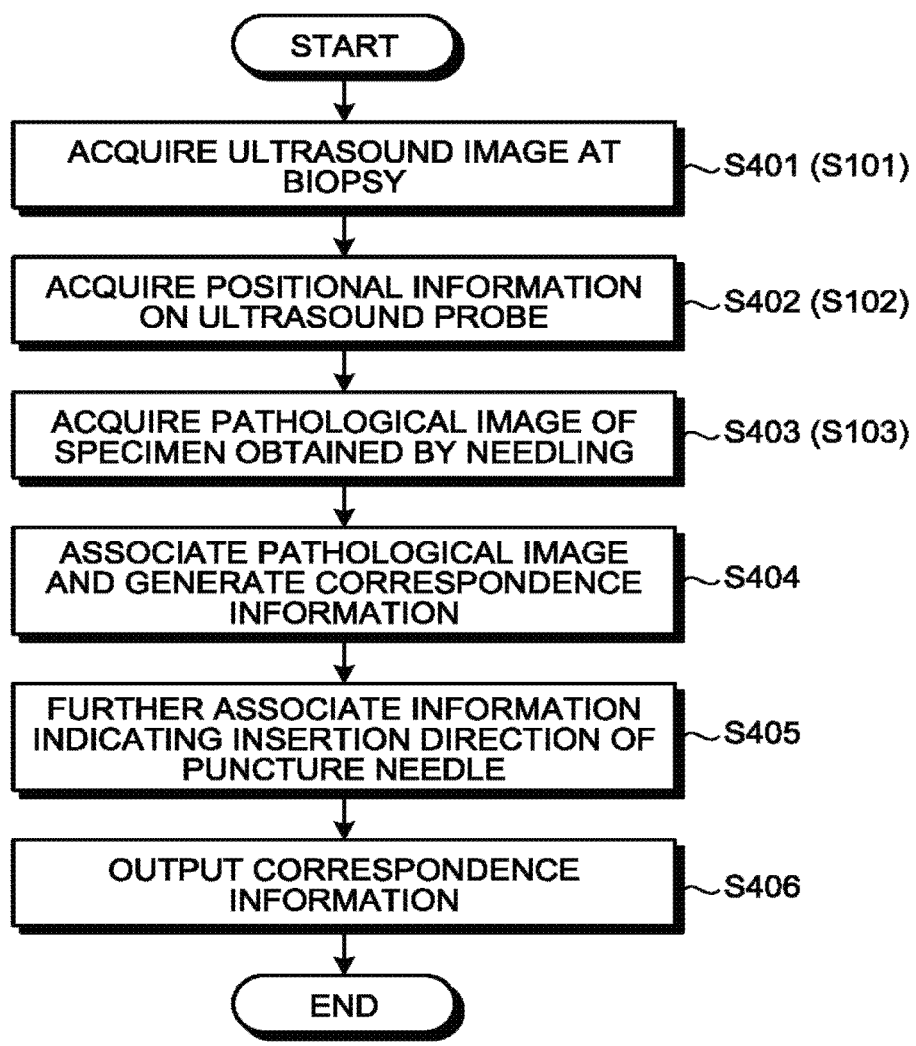
FIG. 20 is a flowchart illustrating a processing procedure of an image processing apparatus according to a modification of the third embodiment.

FIG. 20 is a flowchart illustrating a processing procedure of the image processing apparatus 30 according to a modification of the third embodiment. Step S401 to Step S403 are steps corresponding to the acquisition function 35*a*. The acquisition function 35*a* is implemented at the steps when the processing circuitry 35 invokes a predetermined computer program corresponding to the acquisition function 35*a* from the control program DB 34*d* of the storage 34 and executes the invoked computer program. Step S401 to Step S403 are the same as the processing of Step S101 to Step S103 illustrated in FIG. 7, and hence detailed descriptions thereof are omitted.

Step S404 to Step S406 are steps corresponding to the control function 35*b*. The control function 35*b* is implemented at the steps when the processing circuitry 35 invokes a predetermined computer program corresponding to the control function 35*b* from the control program DB 34*d* of the storage 34 and executes the invoked computer program.

At Step S404, the control function 35*b* associates the pathological image acquired at Step S403 to generate correspondence information. For example, as described above with reference to FIG. 17, the control function 35*b* generates correspondence information in which an ultrasound image including scanning positional information 61 and a pathological image are associated with each other. At Step S405, similarly to Step S308, the control function 35*b* further associates information indicating the insertion direction of the puncture needle 21*b*. For example, as described above with reference to FIG. 18, the control function 35*b* further associates information indicating the insertion direction of the puncture needle 21*b* with correspondence information in which the ultrasound image including the scanning positional information 61 and a pathological image are associated with each other. Then, at Step S406, the control function 35*b* outputs the correspondence information generated at Step S405.

In the modification of the third embodiment, the case where the control function 35*b* causes the display 32 to display an ultrasound image at biopsy having scanning positional information superimposed thereon, a pathological image of a specimen obtained by the biopsy, and puncture needle information in association with one another has been described, but the embodiments are not limited thereto. For example, the control function 35*b* may receive an instruction to turn on and off the display of puncture needle information from the operator through the input interface 31.

As described above, in the modification of the third embodiment, the image processing apparatus 30 acquires an ultrasound image at biopsy, positional information indicating the position of an ultrasound probe in a subject at the biopsy using the ultrasound image, and a pathological image generated after the biopsy based on a specimen obtained by the biopsy. Then, the image processing apparatus 30 generates correspondence information in which the ultrasound image, the pathological image, and the positional information are associated with one another, and causes the display 32 to display the generated correspondence information. Consequently, according to the modification of the third embodiment, for example, the pathologist can easily grasp the correspondence relation between an ultrasound image at biopsy and a pathological image of a specimen obtained by the biopsy. As a result, for a pathological diagnosis using a pathological image, a pathologist can add a finding from an ultrasound image to a finding from the pathological image in consideration of consistency between the ultrasound image and the pathological image, which enables a more accurate diagnosis to be efficiently performed. In addition, the pathologist can write and report a more reliable report to other clinicians.

Reference images described in the first embodiment, the modification of the first embodiment, and the second embodiment may be further associated with the correspondence information generated in the modification of the third embodiment. For example, in the case of further associating a reference image described in the first embodiment or the modification of the first embodiment with correspondence information generated in the modification of the third embodiment, the acquisition function 35*a* further executes the processing of Step S104 illustrated in FIG. 7 to acquire a reference image. Then, for example, the control function 35*b* executes the processing of Step S105 and the processing of Step S106 illustrated in FIG. 7 after the end of the processing of Step S405 illustrated in FIG. 20 to further associate a reference image. For example, in the case of further associating a reference image described in the second embodiment with correspondence information generated in the modification of the third embodiment, the acquisition function 35*a* further executes the processing of Step S204 illustrated in FIG. 13 to acquire a three-dimensional image. Then, for example, the control function 35*b* executes the processing of Step S205 and the processing of Step S206 illustrated in FIG. 13 after the end of the processing of Step S405 illustrated in FIG. 20 to further associate a reference image.

Other Embodiments

The embodiments are not limited to the above-mentioned embodiments.

The control function 35*b* in the above-mentioned embodiments receives the setting of puncture needle information from the operator through the input interface 31, but the embodiments are not limited thereto. For example, the control function 35*b* may extract the puncture needle 21*b* from an ultrasound image. Then, the control function 35*b* sets at least one of the needle tip side and the needle insertion side. For example, in the ultrasound image, the control function 35*b* sets the center side of the body as the needle tip side and the body surface side as the needle insertion side. Information indicating the insertion direction of the puncture needle 21*b* at biopsy may be set in the pathological image creation apparatus 40. In such a case, the pathological image creation apparatus 40 may set puncture needle information on a pathological image, or may add puncture needle information to additional information of a pathological image.

Figure 21:
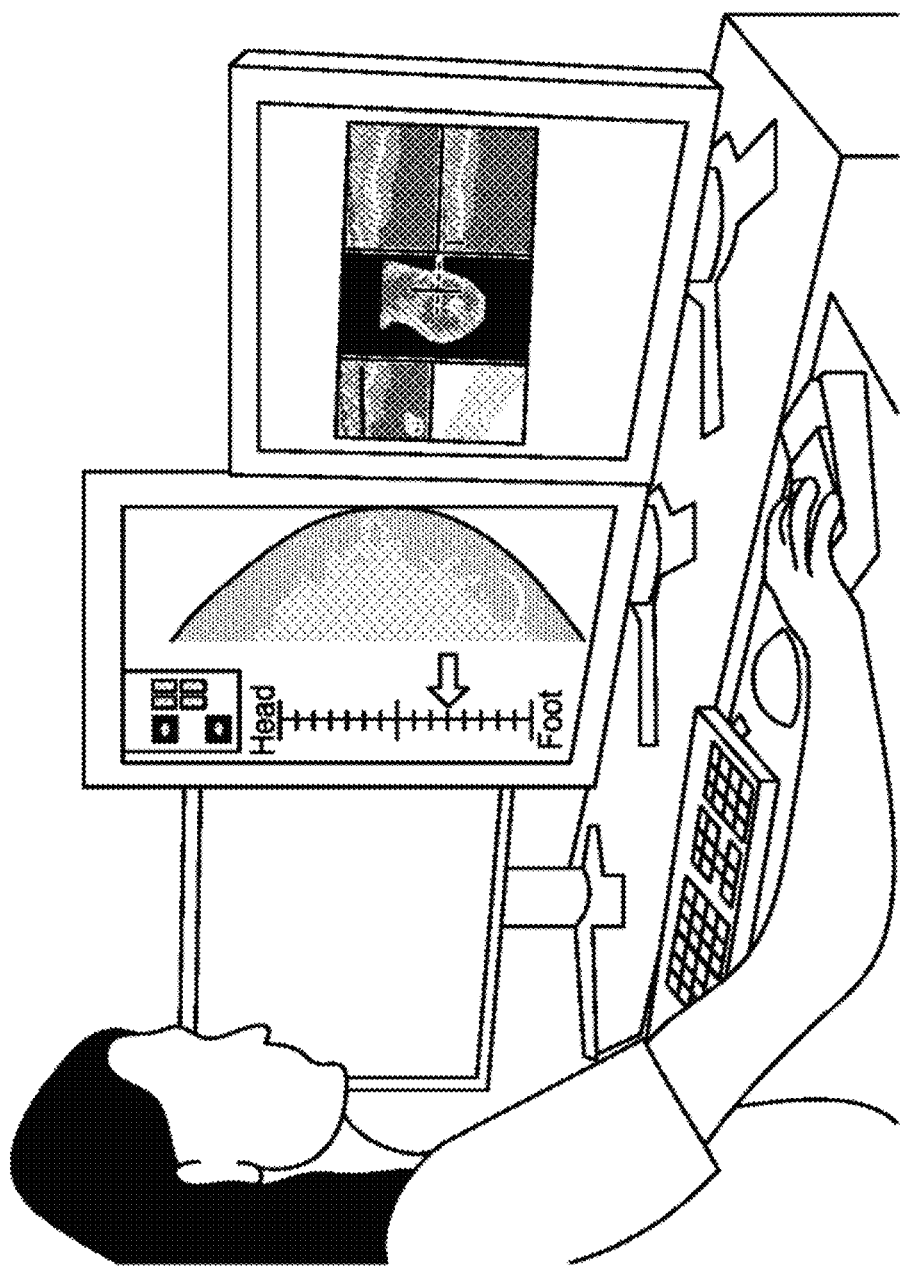
FIG. 21 is a diagram (1) for describing another embodiment.

The control function 35*b* stores the generated correspondence information in the storage 34. Then, the control function 35*b* reads the correspondence information from the storage 34 and causes the display 32 to display the correspondence information in response to an instruction from a pathologist. In such a case, the control function 35*b* may cause the displays 32 to display correspondence information. FIG. 21 is a diagram for describing another embodiment. FIG. 21 illustrates the case where the image processing apparatus 30 is connected to three displays. In the example illustrated in FIG. 21, the control function 35*b* causes the right display 32 to display the correspondence information illustrated in FIG. 15, the center display 32 to display a CC image as a reference image, and the left display 32 to display nothing. The control function 35*b* may switch a combination of correspondence information displayed on the displays 32 in response to an operation from the operator. For example, the control function 35*b* may switch a three-dimensional ultrasound image to a tomosynthesis image, a CC image, or an MLO image in the correspondence information displayed on the right display 32. The control function 35*b* may cause the display 32 of the image processing apparatus 30 and a display of a portable terminal used by a pathologist to display the same correspondence information.

Figure 22:
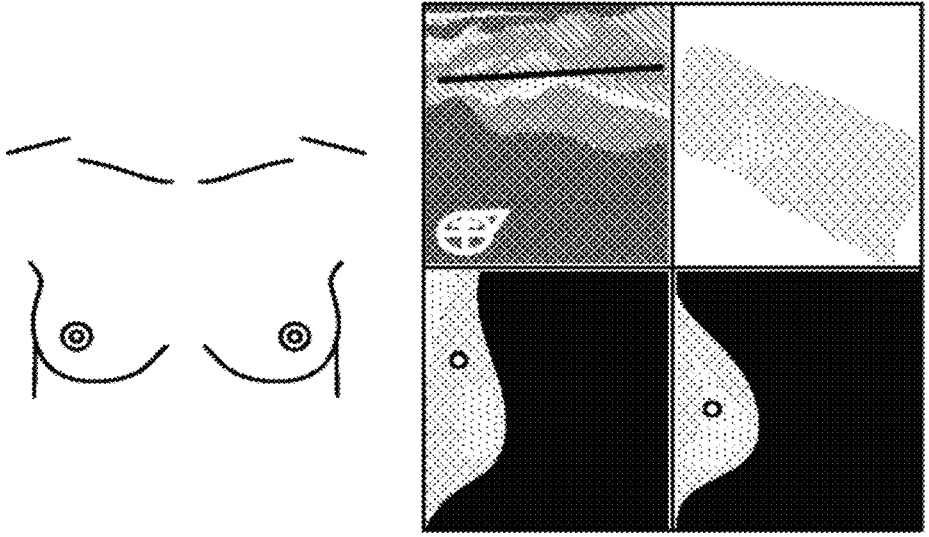
FIG. 22 is a diagram (2) for describing another embodiment.

In the above-mentioned embodiments, the control function 35*b* causes the display 32 to display correspondence information, but the embodiments are not limited thereto. For example, the control function 35*b* may generate pathological diagnosis request including correspondence information. FIG. 22 is a diagram for describing other embodiments. Referring to FIG. 22, the case of generating a mammary gland pathological tissue diagnosis request as an example of a pathological diagnosis request is described.

At the top of the pathological diagnosis request illustrated in FIG. 22, items for inputting the subject name, the date of birth, and the sex as subject information are provided. A schematic diagram of breasts is provided on the left side in the middle of the pathological diagnosis request illustrated in FIG. 22. Then, an input position of correspondence information is provided on the right side in the middle of the pathological diagnosis request illustrated in FIG. 22. For example, the control function 35*b* generates a pathological diagnosis request in which the correspondence information illustrated in FIG. 11 is inserted to the input position of the correspondence information. Then, the control function 35*b* causes the display 32 to display the generated pathological diagnosis request.

In the above-mentioned embodiments, the control function 35*b* causes the display 32 to display correspondence information and a pathological diagnosis request including the correspondence information, but the embodiments are not limited thereto. For example, the control function 35*b* may cause a printer to print correspondence information and a pathological diagnosis request including the correspondence information, or may cause an information processing apparatus used by a pathologist to transmit correspondence information and a pathological diagnosis request including the correspondence information. In other words, the control function 35*b* causes a predetermined output unit to output correspondence information and a pathological diagnosis request including the correspondence information.

In the above-mentioned embodiments, correspondence information in which an ultrasound image at biopsy, a pathological image, and scanning positional information are associated with one another is generated and displayed for pathological diagnosis in breast cancer clinical practice, but the embodiments are not limited thereto. For example, the above-mentioned embodiments are applicable also to pathological diagnosis of other sites such as the head, chest, abdomen, and lower extremity. In other words, the observation target is not limited to a breast, and may be other sites such as the head, chest, abdomen, and lower extremity. In such a case, the storage 24*f* stores therein body marks corresponding to sites, and scanning positional information in which the position of the ultrasound probe 21 obtained when the site of the subject P is scanned is associated is generated on the body mark.

In the above-mentioned embodiments, the image DB 34*a* stores ultrasound images, mammography images, and pathological images therein, and the acquisition function 35*a* acquires the ultrasound images, the mammography images, and the pathological images from the image DB 34*a*. However, the embodiments are not limited thereto. For example, when the image DB 34*a* does not store mammography images therein, the acquisition function 35*a* may communicate with the mammography apparatus 10 through the communication control interface 33 to acquire mammography images, and store the acquired mammography images in the image DB 34*a*. For example, when the image DB 34*a* does not store ultrasound images therein, the acquisition function 35*a* communicates with the ultrasound diagnosis apparatus 20 through the communication control interface 33 to acquire ultrasound images, and stores the acquired ultrasound images in the image DB 34*a*. For example, when the image DB 34*a* does not store pathological images therein, the acquisition function 35*a* communicates with the pathological image creation apparatus 40 through the communication control interface 33 to acquire pathological images, and stores the acquired pathological images in the image DB 34*a*.

In the above-mentioned embodiments, the control function 35*b* generates and displays correspondence information in which an ultrasound image corresponding to single biopsy is associated with a reference image. However, the embodiments are not limited thereto. For example, the control function 35*b* may generate and display correspondence information in which ultrasound images corresponding to biopsies are associated with reference images. Specifically, the control function 35*b* generates correspondence information further associated with an ultrasound image at a biopsy by which a specimen is collected from an observation target at a timing different from the first biopsy, based on positional information, and causes the display 32 to display the generated correspondence information.

Figure 23:
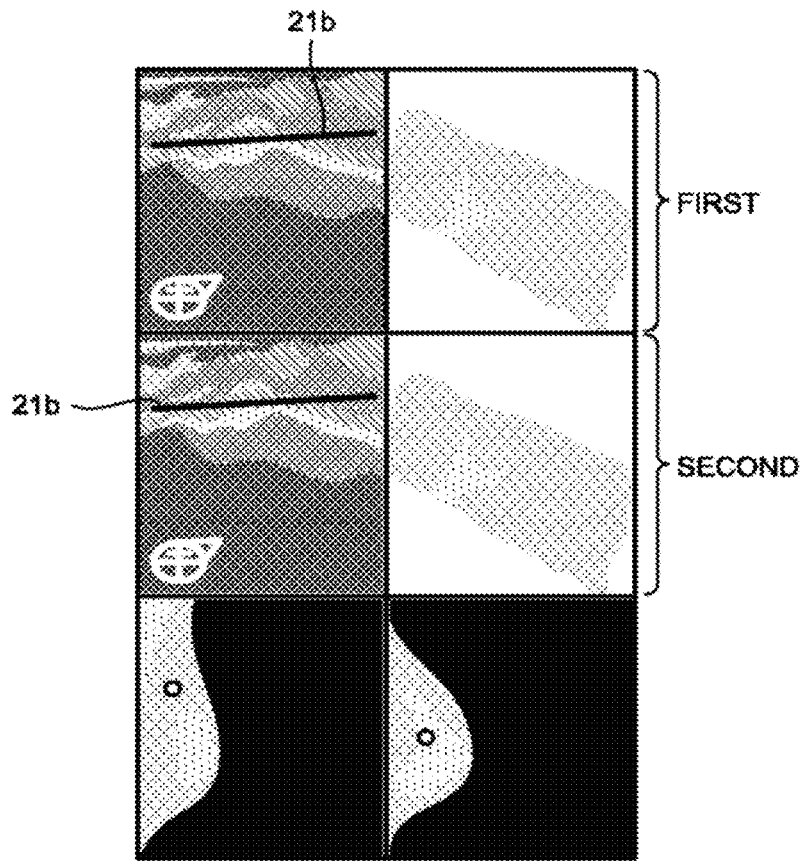
FIG. 23 is a diagram (3) for describing another embodiment.

FIG. 23 is a diagram for describing another embodiment. For example, as illustrated in FIG. 23, the control function 35*b* generates and displays correspondence information in which an ultrasound image and a pathological image at the first biopsy are arranged at the top, an ultrasound image and a pathological image at the second biopsy are arranged in the middle, and reference images are arranged at the bottom. In this case, the acquisition function 35a further acquires an ultrasound image at the second biopsy by which a specimen is collected from an observation target at a timing different from that for the first biopsy.

The observation target is the same between the first biopsy and the second biopsy, and hence the same scanning positional information is superimposed. The method for displaying ultrasound images corresponding to biopsies is not limited to the one illustrated in FIG. 23. For example, the control function 35b may display an ultrasound image and a pathological image while switching the ultrasound image and the pathological image at the first biopsy and the ultrasound image and the pathological image at the second biopsy in response to an operation received through the input interface 31.

In the above-mentioned embodiments, the control function 35b generates correspondence information in which an ultrasound image at biopsy and a reference image are associated with each other. However, the embodiments are not limited thereto. For example, the control function 35b may generate correspondence information in which an ultrasound image obtained when a procedure other than biopsy is performed or an ultrasound image that has been operated and a reference image are associated with each other.

In such a case, the acquisition function 35a acquires an ultrasound image by determining information indicating a procedure other than biopsy and information on operations for an ultrasound image as additional information. For example, the acquisition function 35a acquires, as an ultrasound image having information indicating a procedure other than biopsy, an ultrasound image obtained when a metal marker for detecting the position of a tumor is placed. For example, the acquisition function 35a acquires, as an ultrasound image having information on operations for the ultrasound image, an ultrasound image in which an ROI is set, an ultrasound image subjected to measurement, an ultrasound image given with annotations, an ultrasound image given with diagnosis results by computer-aided diagnosis (CAD), or an ultrasound image described in a report. The acquisition function 35a acquires each of the above-mentioned ultrasound images based on subject information associated with IDs or information included in tags of DICOM.

Figure 24:
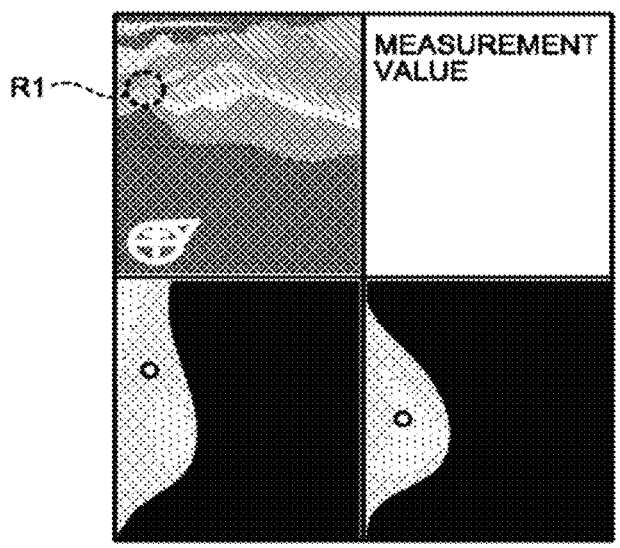
FIG. 24 is a diagram (4) for describing another embodiment.

Then, the control function 35b generates correspondence information in which the ultrasound image and the reference image acquired by the acquisition function 35a are associated with each other, and causes the display 32 to display the generated correspondence information. FIG. 24 is a diagram for describing another embodiment. For example, as illustrated in FIG. 24, the control function 35b generates correspondence information in which an ultrasound image including scanning positional information obtained when a region of interest R1 is placed is arranged on the upper left side, an MLO image specified as a reference image is arranged on the lower left side, and a CC image specified as a reference image is arranged on the lower right side. For example, in the case where measurement processing has been performed on the region of interest R1, the control function 35b generates correspondence information in which the measurement result is further associated as illustrated on the upper right side in FIG. 24.

As described above, the image processing apparatus 30 can generate and display correspondence information in which a reference image is associated with not only an ultrasound image at biopsy but also ultrasound images provided with various kinds of additional information.

In the above-mentioned embodiments, the image processing apparatus 30 in the medical information processing system 100 executes various kinds of processing. However, the embodiments are not limited thereto, and various kinds of processing may be executed by another apparatus in the medical information processing system 100. In one example, the ultrasound diagnosis apparatus 20 may execute various kinds of processing described above. In such a case, the storage 24f stores therein computer programs corresponding to the acquisition function 35a and the control function 35b described above. Then, the processing circuitry 24h executes computer programs read from the storage 24f to implement the functions corresponding to the computer programs.

The ultrasound diagnosis apparatus 20 may have an echo scan guide function. Specifically, the ultrasound diagnosis apparatus 20 can convert the position of a finding registered on a mammography image into a position on a body mark on ultrasound waves. Specifically, the processing circuitry 24h can acquire conversion information by converting the position of a region of interest in a reference image into a position on a schematic diagram. Then, the processing circuitry 24h uses the positional information and the conversion information to specify the reference image to be associated with the correspondence information.

Accordingly, for example, the ultrasound diagnosis apparatus 20 can generate correspondence information by acquiring conversion information in real time during biopsy in addition to conversion information already acquired. In such a case, the processing circuitry 24h uses the echo scan guide function to acquire conversion information from a mammography image. The processing circuitry 24h further specifies, based on positional information on an ultrasound image collected at biopsy and conversion information, a reference image corresponding to the ultrasound image at the biopsy, and generates correspondence information in which the specified reference image and the ultrasound image at the biopsy are associated with each other.

The processing circuitry 24h can specify a reference image corresponding to an ultrasound image at the past biopsy by using the echo scan guide function to acquire conversion information from a mammography image. Specifically, the processing circuitry 24h acquires a mammography image provided with the same subject ID as a subject ID of a past ultrasound image, and acquires conversion information from the acquired mammography image. Then, the processing circuitry 24h specifies a reference image corresponding to the past ultrasound image based on positional information on the past ultrasound image and the acquired conversion information.

The term "processor" used in the above description means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor implements functions by reading and executing computer programs stored in the control program DB 34d of the storage 34. A computer program may be directly incorporated in a circuit of the processor instead of storing a computer program in the control program DB 34d of the storage 34. In this case, the processor implements functions by reading and executing computer programs incorporated in the circuit. Each processor in the present embodiment is not limited to the case where the processor is configured as a single circuit. Independent circuits may be combined and configured as a single processor to implement the functions.

The components in FIG. 5 may be integrated into a single processor to implement the functions.

In the description of the above-mentioned embodiments, the components of the illustrated apparatus are conceptually illustrative based on their functions, and are not necessarily required to be physically configured as illustrated. In other words, a specific mode for dispersion and integration of the apparatus is not limited to the illustrated one, and all or part of the apparatus can be functionally or physically dispersed and integrated in any unit depending on various kinds of loads, usage conditions, and any other parameter. In addition, all or any part of the processing functions executed by the apparatus may be implemented by a CPU and computer programs analyzed and executed by the CPU, or implemented as hardware by wired logic.

The control method described in the above-mentioned embodiments can be implemented by a computer such as a personal computer and a workstation executing a control program prepared in advance. The control program can be distributed through a network such as the Internet. The control program can be recorded in a computer-readable recording medium, such as a hard disk, a flexible disk (ED), a CD-ROM, an MO, and a DVD, and executed by a computer reading the control program from the recording medium.

According to at least one of the embodiments described above, diagnosis with higher precision can be efficiently performed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system comprising: processing circuitry configured to
    select an ultrasound image including an observation target and having additional information from a plurality of ultrasound images by determining whether or not the additional information is stored in data of the ultrasound image, the additional information including information indicating that an image is an ultrasound image collected when a procedure is performed on the observation target and being stored in data of the ultrasound image,
    acquire positional information indicating a position of an ultrasound probe in contact with a subject at time of collection of the selected ultrasound image, and a plurality of reference images obtained by taking an image of a region including the observation target at a time point other than the time of collection, the positional information being information indicating, on a schematic diagram, the position of the ultrasound probe at the time of collection of the ultrasound image collected when the procedure is performed on the observation target,
    obtain conversion information indicating a position of a region of interest in a reference image on the schematic diagram for each of the plurality of reference images,
    identify, based on the positional information and the conversion information, a relative position between the position of the ultrasound probe at the time of collecting the ultrasound image collected when the procedure is performed on the observation target and the position of a region of interest in the reference image for each of the plurality of reference images,
    identify, based on the identified relative position, two or more reference images associated with first correspondence information from the plurality of reference images,
    set priorities for the identified two or more reference images based on the position of the region of interest in the conversion information and the position of the ultrasound probe in the positional information,
    generate the first correspondence information in which the selected ultrasound image and the identified two or more reference images are associated with each other,
    cause a display to output the selected ultrasound image and one set of the identified two or more reference images based on the generated first correspondence information,
    receive an instruction to switch the displayed one set of the identified two or more reference images from an operator, and
    use the priorities to change the displayed one set of the identified two or more reference images to another set of the identified two or more reference images.

2. The medical information processing system according to claim 1, wherein the processing circuitry is configured to
    select an ultrasound image at biopsy for collecting a specimen from the observation target by determining whether or not the additional information is stored in data of the ultrasound image,
    acquire positional information indicating a position of an ultrasound probe in contact with a subject at the biopsy using the ultrasound image, and a plurality of reference images obtained by taking an image of a region including the observation target at a time point other than the biopsy, and
    generate second correspondence information in which the ultrasound image at the biopsy and the two or more reference images are associated with each other.

3. The medical information processing system according to claim 1, wherein the processing circuitry is configured to set priorities in ascending order of distance between the position of the region of interest in the conversion information and the position of the ultrasound probe in the positional information, and associate the identified two or more reference images with the selected ultrasound image in order of priority and causes the display to output the selected ultrasound image and the identified reference image in an order of priority.

4. The medical information processing system according to claim 2, wherein the processing circuitry is configured to obtain, when the plurality of reference images obtained by taking an image of a region including the observation target at a time point other than the biopsy are three-dimensional images, an image of a cross section corresponding to the position of the ultrasound probe based on the positional information for each of the plurality of reference images obtained by taking an image of a region including the observation target at a time point other than the biopsy, and associate the obtained images with the selected ultrasound image at biopsy.

5. The medical information processing system according to claim 4, wherein the processing circuitry is configured to calculate, from the ultrasound image at the biopsy, a distance from a body surface to a needling position, and specify a cross section corresponding to a three-dimensional image based on calculated distance information.

6. The medical information processing system according to claim 2, wherein the processing circuitry is configured to
further acquire a pathological image generated after the biopsy based on the specimen obtained by the biopsy, and
cause the display to output the pathological image further associated with the second correspondence information.

7. The medical information processing system according to claim 6, wherein the processing circuitry is configured to cause the display to output information indicating an insertion direction of a puncture needle at the biopsy further associated with the second correspondence information.

8. The medical information processing system according to claim 1, wherein
the medical information processing system is connected to a plurality of displays serving as the display, and
the processing circuitry is configured to cause the display to display the selected ultrasound image and the identified reference image.

9. The medical information processing system according to claim 2, wherein the processing circuitry is configured to generate a pathological diagnosis request including the second correspondence information, and cause the display to output the generated pathological diagnosis request.

10. The medical information processing system according to claim 2, wherein the processing circuitry is configured to
further select an ultrasound image at a second biopsy by which a second specimen is collected from the observation target at a timing different from the time of image collection by determining whether or not the additional information is stored in data of the ultrasound image,
generate, based on the positional information, correspondence information further associated with the ultrasound image at the second biopsy by which the second specimen is collected from the observation target at the timing different from the time of image collection, and
cause the display to output the generated correspondence information.

11. The medical information processing system according to claim 1, wherein the processing circuitry is configured to acquire the ultrasound image by determining information indicating a procedure for the observation target and information on operations for the ultrasound image as the additional information.

12. A medical image processing apparatus comprising:
processing circuitry configured to
select an ultrasound image including an observation target and having additional information from a plurality of ultrasound images by determining whether or not the additional information is stored in data of the ultrasound image, the additional information including information indicating that an image is an ultrasound image collected when a procedure is performed on the observation target and being stored in data of the ultrasound image,
acquire positional information indicating a position of an ultrasound probe in contact with a subject at time of collection of the selected ultrasound image, and a plurality of reference images obtained by taking an image of the observation target at a time point other than the time of collection, the positional information being information indicating, on a schematic diagram, the position of the ultrasound probe at the time of collection of the ultrasound image collected when the procedure is performed on the observation target,
obtain conversion information indicating a position of a region of interest in a reference image on the schematic diagram for each of the plurality of reference images,
identify, based on the positional information and the conversion information, a relative position between the position of the ultrasound probe at the time of collecting the ultrasound image collected when the procedure is performed on the observation target and the position of a region of interest in the reference image for each of the plurality of reference images,
identify, based on the identified relative position, two or more reference images associated with correspondence information from the plurality of reference images,
set priorities for the identified two or more reference images based on the position of the region of interest in the conversion information and the position of the ultrasound probe in the positional information,
generate the correspondence information in which the selected ultrasound image and the identified two or more reference images are associated with each other, and
cause a display to output the selected ultrasound image and one set of the identified two or more reference images based on the generated correspondence information,
receive an instruction to switch the displayed one set of the identified two or more reference images from an operator, and
use the priorities to change the displayed one set of the identified two or more reference images to another set of the identified two or more reference images.

13. A medical information processing system comprising:
processing circuitry configured to
select an ultrasound image including an observation target and having additional information from a plurality of ultrasound images by determining whether or not the additional information is stored in data of the ultrasound image, the additional information indicating that an image is an ultrasound image collected when a biopsy is performed on an observation target and being stored in data of the ultrasound image,
acquire positional information indicating a position of an ultrasound probe in contact with a subject at the biopsy using the selected ultrasound image, a plurality of reference images obtained by taking an image of a region including the observation target at a time point other than the time of the biopsy, and a pathological image generated after the biopsy based on a specimen obtained by the biopsy, the positional information being information indicating, on a schematic diagram, the position of the ultrasound probe at a time of collecting the ultrasound image collected when the biopsy is performed on the observation target, obtain conversion information indicating a position of a region of interest in a reference image on the schematic diagram for each of the plurality of reference images, identify, based on the positional information and the conversion information, a relative position between the position of the ultrasound probe at the time of collecting the ultrasound image collected when a procedure is performed on the observation target and the position of a region of interest in the reference image for each of the plurality of reference images, identify, based on the identified relative position, two or more reference images associated with correspondence information from the plurality of reference images, set priorities for the identified two or more reference images based on the position of the region of interest in the conversion information and the position of the ultrasound probe in the positional information, generate correspondence information in which the selected ultrasound image at the biopsy, the identified two or more reference images, and the pathological image are associated with one another, cause a display to output the selected ultrasound image, one set of the identified two or more reference images, and the pathological image based on the generated correspondence information, receive an instruction to switch the displayed one set of the identified two or more reference images from an operator, and use the priorities to change the displayed one set of the identified two or more reference images to another the identified two or more reference images without changing the selected ultrasound image and the pathological image.

* * * * *